US012622919B2

(12) United States Patent
Chen et al.

(10) Patent No.: US 12,622,919 B2
(45) Date of Patent: May 12, 2026

(54) **METHODS FOR TREATING HYPERVIRULENT *KLEBSIELLA PNEUMONIAE* INFECTION**

(71) Applicant: City University of Hong Kong, Hong Kong (CN)

(72) Inventors: Sheng Chen, Hong Kong (CN); Guan Yang, Hong Kong (CN); Qi Xu, Hong Kong (CN); Xiaoxuan Liu, Hong Kong (CN)

(73) Assignee: City University of Hong Kong, Hong Kong (CN)

( * ) Notice: Subject to any disclaimer, the term of this patent is extended or adjusted under 35 U.S.C. 154(b) by 0 days.

(21) Appl. No.: 18/188,541

(22) Filed: Mar. 23, 2023

(65) Prior Publication Data

US 2024/0316068 A1 Sep. 26, 2024

(51) Int. Cl.
| | |
|---|---|
| *A61K 31/353* | (2006.01) |
| *A61K 31/341* | (2006.01) |
| *A61K 31/52* | (2006.01) |
| *A61K 31/545* | (2006.01) |
| *A61K 31/616* | (2006.01) |
| *A61P 31/04* | (2006.01) |

(52) U.S. Cl.
CPC .......... *A61K 31/616* (2013.01); *A61K 31/341* (2013.01); *A61K 31/353* (2013.01); *A61K 31/52* (2013.01); *A61K 31/545* (2013.01); *A61P 31/04* (2018.01)

(58) Field of Classification Search
CPC .. A61K 31/616; A61K 31/341; A61K 31/353; A61K 31/52; A61K 31/545; A61P 31/04
See application file for complete search history.

(56) References Cited

U.S. PATENT DOCUMENTS

| | | | |
|---|---|---|---|
| 2012/0093738 A1* | 4/2012 | Pilgaonkar ........... | A61K 9/2081 424/44 |
| 2021/0322396 A1* | 10/2021 | Kohane .................... | A61P 27/16 |
| 2022/0296594 A1* | 9/2022 | Yang ...................... | A61K 45/06 |

OTHER PUBLICATIONS

Avycaz FDA Revised Jun. 2016 (Year: 2016).*
Aspirin FDA 2013 (Year: 2013).*
"Guidelines for the prevention and control of carbapenem-resistant Enterobacteriaceae, Acinetobacter baumannii and Pseudomonas aeruginosa in health care facilities" Geneva: World Health Organization; 2017. License: CC BY-NC-SA 3.0 IGO (Year: 2017).*
Tangden 2014 J Int Med 277 5 501 (Year: 2014).*
Wu et al Clin Microbiol Rev 2019 32 2 (Year: 2019).*
Huang et al Cell Immunol 2021 18 9 2114 (Year: 2021).*
Yong Antimicrobial Agents and Chemotherapy 2012 56 12 6154 (Year: 2012).*

Choby et. al. "Hypervirulent Klebsiella pneumoniae—clinical and molecular perspectives" JIM, 2020, 287, 3, 283-300. DOI: 10.1111/joim.13007 Published online Nov. 2, 2019 (Year: 2019).*
Lee et. al. "Aspirin enhances opsonophagocytosis and is associated to a lower risk for Klebsiella pneumoniae invasive syndrome" BMC Infectious Diseases, 2014, 12, 47, 1-7 DOI: 10.1186/1471-2334-14-47 (Year: 2014).*
Paczosa, M. K. & Mecsas, J. Klebsiella pneumoniae: going on the offense with a strong defense. Microbiology and Molecular Biology Reviews 80, 629-661 (2016).
Marr, C. M. & Russo, T. A. Hypervirulent Klebsiella pneumoniae: a new public health threat. Expert review of anti-infective therapy 17, 71-73 (2019).
Xie, M. et al. Clinical evolution of ST11 carbapenem resistant and hypervirulent Klebsiella pneumoniae. Communications Biology 4, 650, doi: 10.1038/s42003-021-02148-4 (2021).
Anand, T. et al. Phage therapy for treatment of virulent Klebsiella pneumoniae infection in a mouse model. Journal of global antimicrobial resistance 21, 34-41 (2020).
Xu, C. et al. Imidazole type antifungal drugs are effective colistin adjuvants that resensitize colistin-resistant enterobacteriaceae. Advanced Therapeutics 3, 2000084 (2020).
Xiong, H. et al. Innate lymphocyte/Ly6Chi monocyte crosstalk promotes Klebsiella pneumoniae clearance. Cell 165, 679-689 (2016).
Theilgaard-Mönch, K. et al. Haptoglobin is synthesized during granulocyte differentiation, stored in specific granules, and released by neutrophils in response to activation. Blood 108, 353-361 (2006).
Lewis, A. J., Seymour, C. W. & Rosengart, M. R. Current murine models of sepsis. Surgical infections 17, 385-393 (2016).
Genin, M., Clement, F., Fattaccioli, A., Raes, M. & Michiels, C. M1 and M2 macrophages derived from THP-1 cells differentially modulate the response of cancer cells to etoposide. BMC cancer 15, 1-14 (2015).
Murray, P. J. Macrophage polarization. Annual review of physiology 79, 541-566 (2017).
Lawrence, T. & Natoli, G. Transcriptional regulation of macrophage polarization: enabling diversity with identity. Nature reviews immunology 11, 750-761 (2011).
Luu, K. et al. STAT1 plays a role in TLR signal transduction and inflammatory responses. Immunology and cell biology 92, 761-769 (2014).
Rudnicka, L. et al. Cyclosporine therapy during the COVID-19 pandemic. Journal of the American Academy of Dermatology 83, e151-e152 (2020).
Hider, R. C. & Kong, X. Chemistry and biology of siderophores. Natural product reports 27, 637-657 (2010).
Xu, Q., Yang, X., Chan, E. W. C. & Chen, S. The hypermucoviscosity of hypervirulent K. pneumoniae confers the ability to evade neutrophil-mediated phagocytosis. Virulence 12, 2050-2059, doi: 10.1080/21505594.2021.1960101 (2021).

(Continued)

*Primary Examiner* — Kortney L. Klinkel
*Assistant Examiner* — Sophia Reilly
(74) *Attorney, Agent, or Firm* — S&F/WEHRW

(57) ABSTRACT

Methods of treating a hypervirulent *Klebsiella pneumoniae* (hvKp) infection in a subject in need thereof, the method involving co-administering a therapeutically effective amount of an antibiotic and a non-steroidal anti-inflammatory drug or a signal transducer and activator of transcription 1 inhibitor to the subject.

11 Claims, 37 Drawing Sheets

(56) References Cited

OTHER PUBLICATIONS

Manne, B. K. et al. Platelet gene expression and function in patients with COVID-19. Blood 136, 1317-1329 (2020).

Trauer, J. et al. Quantifying the effects of prior acetyl-salicylic acid on sepsis-related deaths: an individual patient data meta-analysis using propensity matching. Critical care medicine 45, 1871 (2017).

Ouyang, Y., Wang, Y., Liu, B., Ma, X. & Ding, R. Effects of antiplatelet therapy on the mortality rate of patients with sepsis: a meta-analysis. Journal of critical care 50, 162-168 (2019).

Herzig, D. et al. STAT1-deficient mice are resistant to CLP-induced septic shock. Shock (Augusta, GA.) 38, 395 (2012).

Yang, G. et al. Pik3c3 deficiency in myeloid cells imparts partial resistance to experimental autoimmune encephalomyelitis associated with reduced IL-1β production. Cellular & Molecular Immunology 18, 2024-2039 (2021).

* cited by examiner a
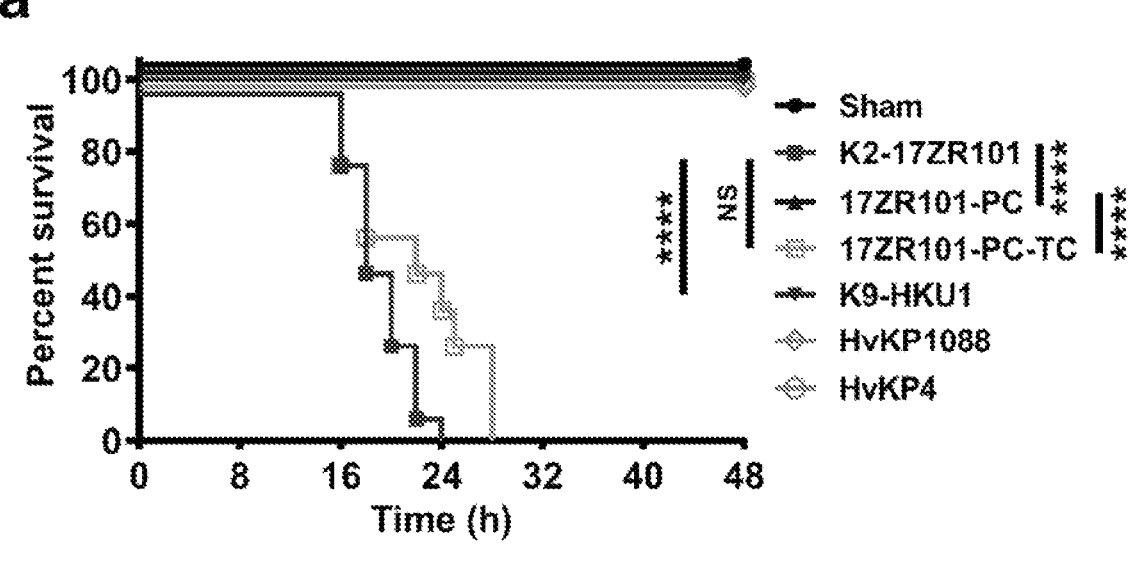
b
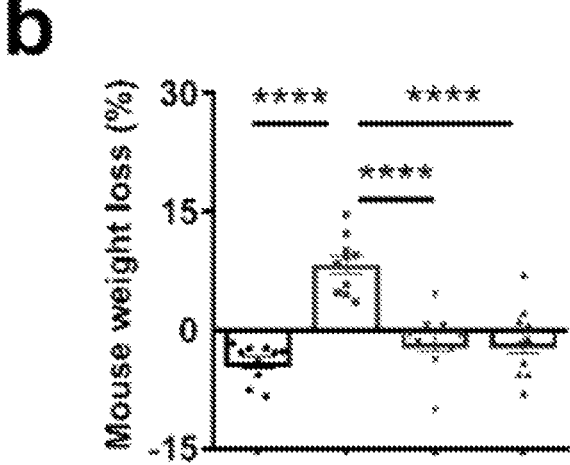
FIG. 1

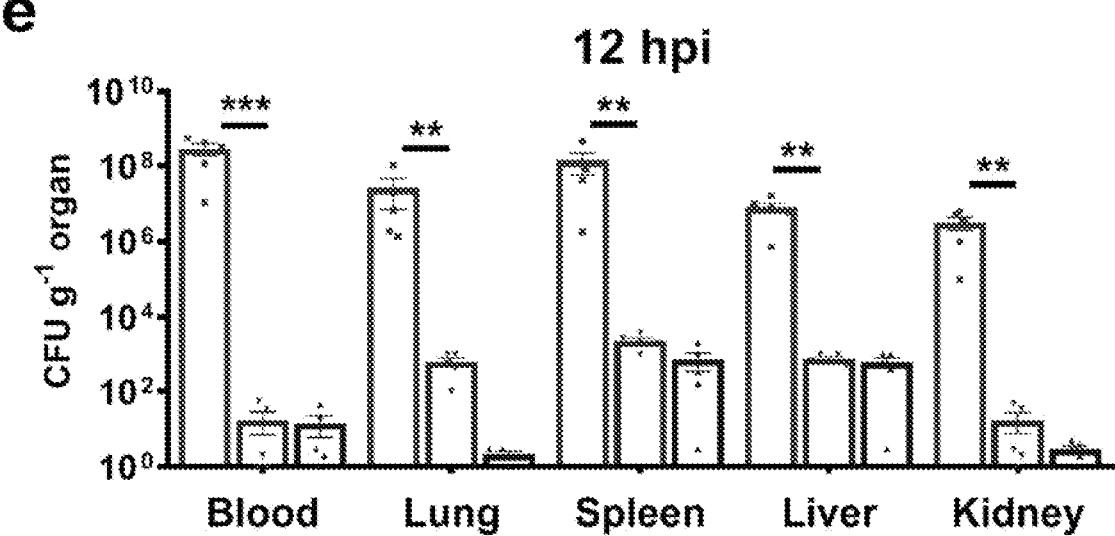
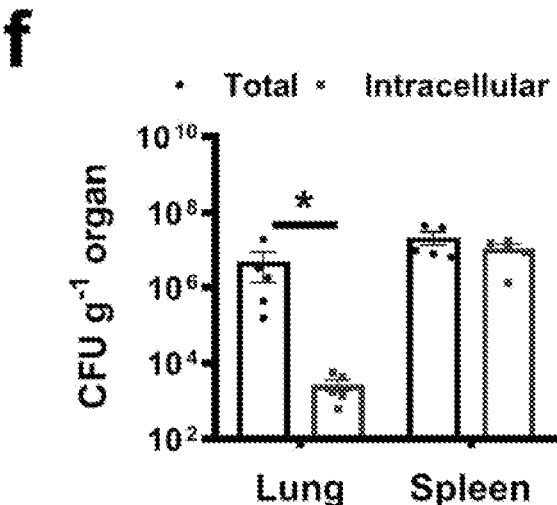
FIG. 1 (Continued)

C

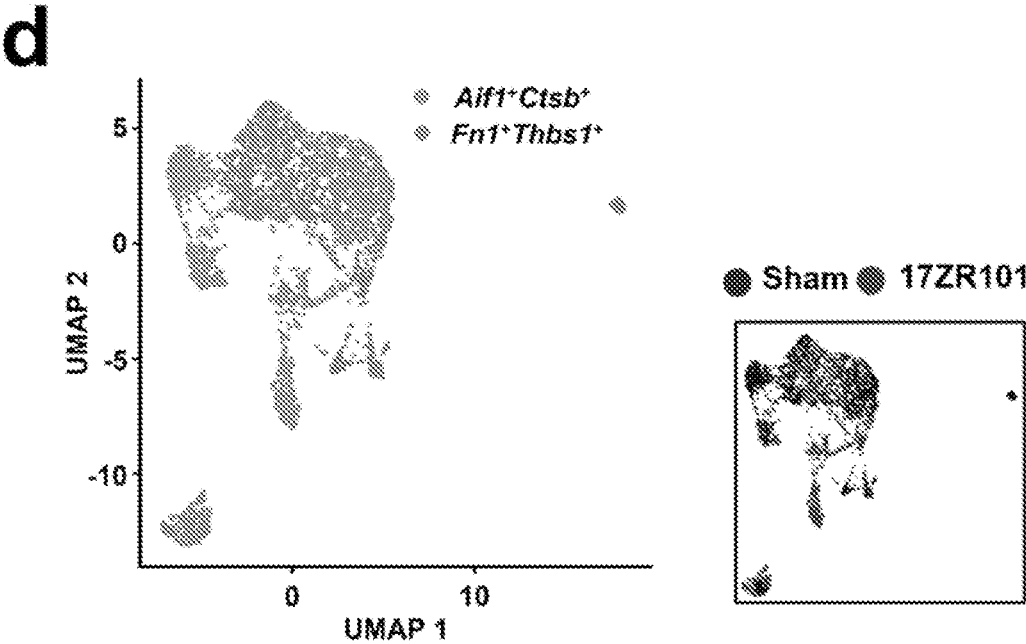
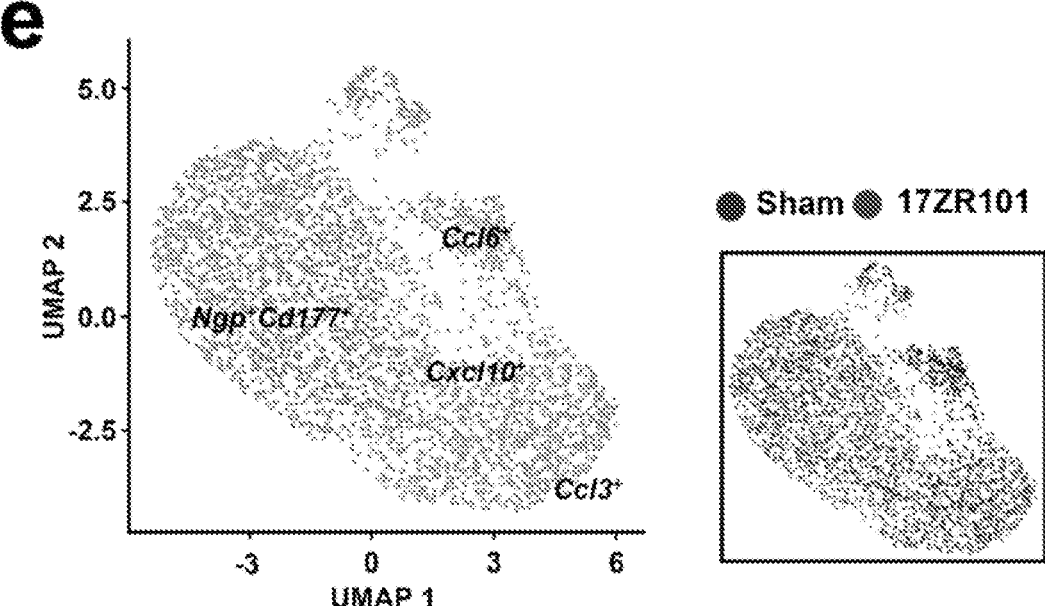
FIG. 2 (Continued)

a b

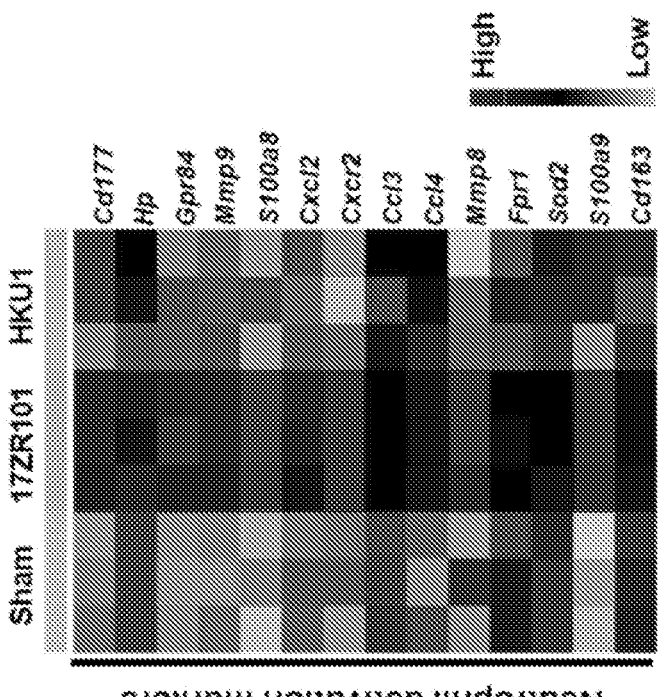
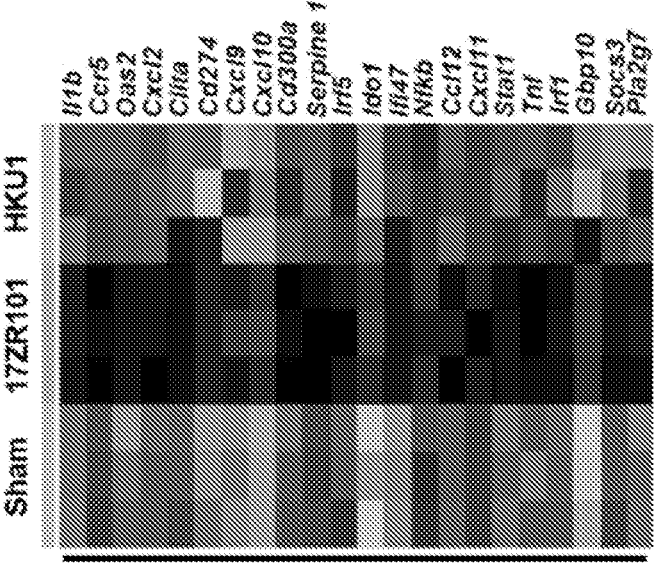
FIG. 3 (Continued)

f

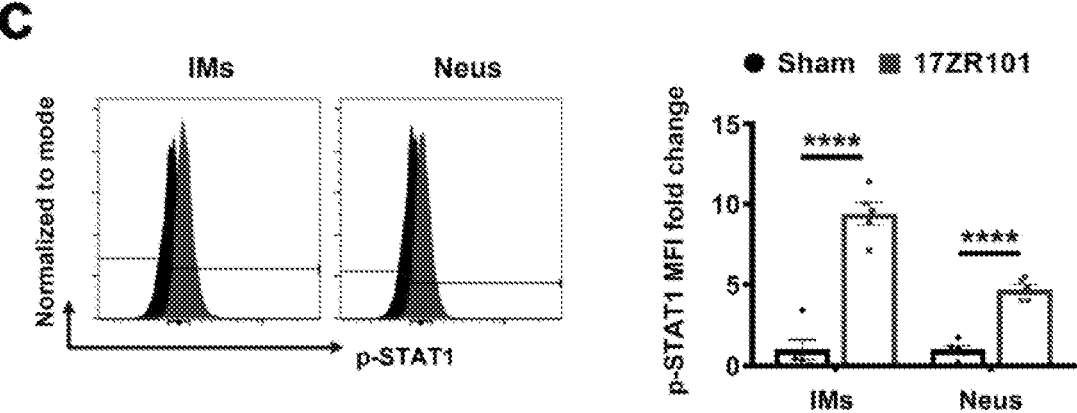
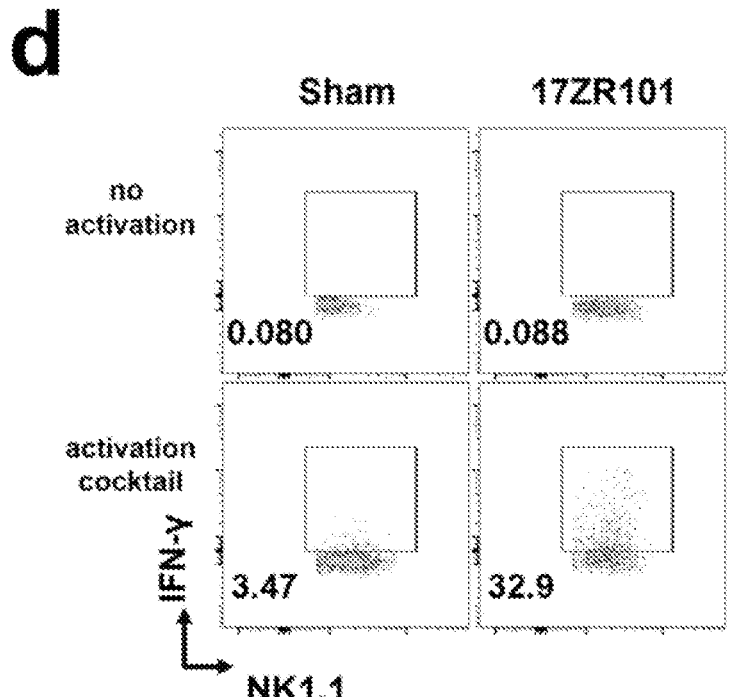
FIG. 4 (Continued)

e
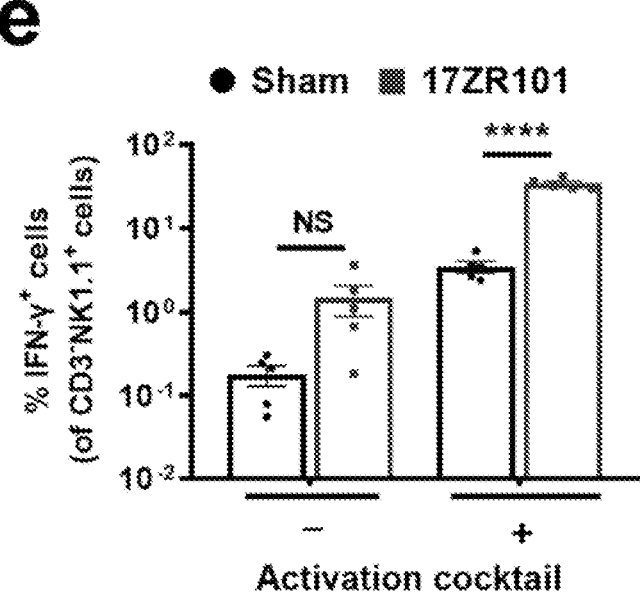
f
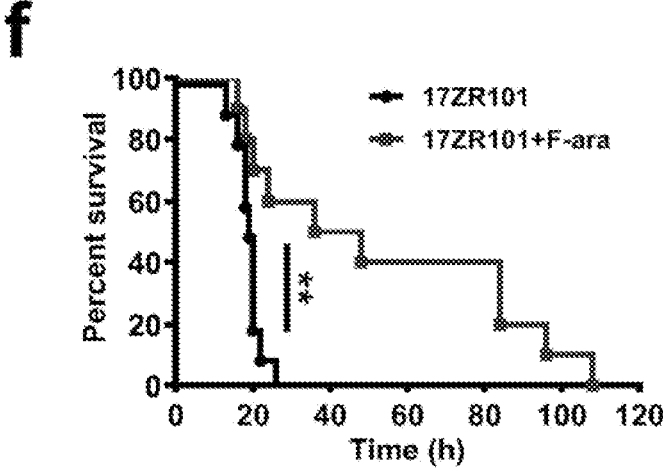
FIG. 4 (Continued)

C e f
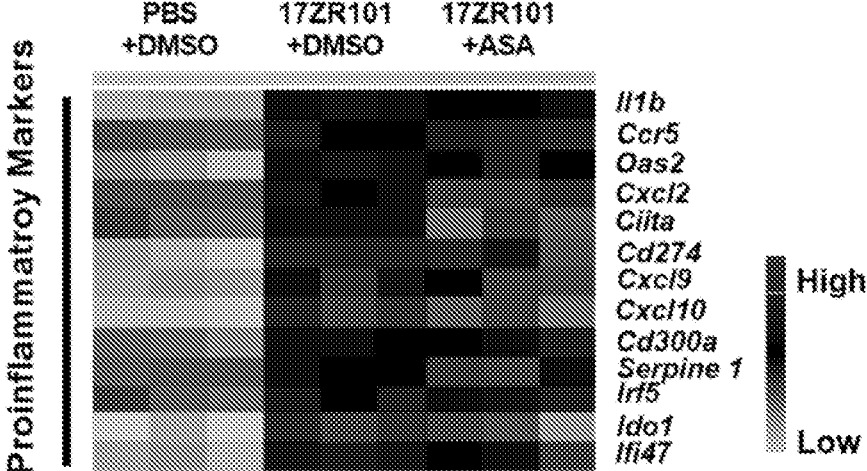
g
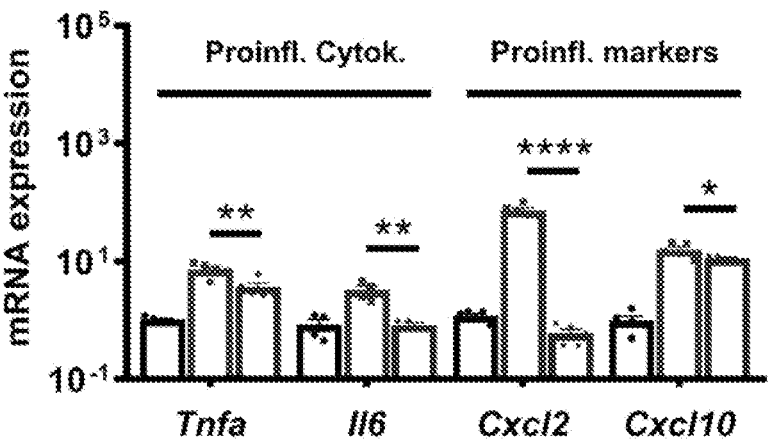
FIG. 5 (Continued)

h a b
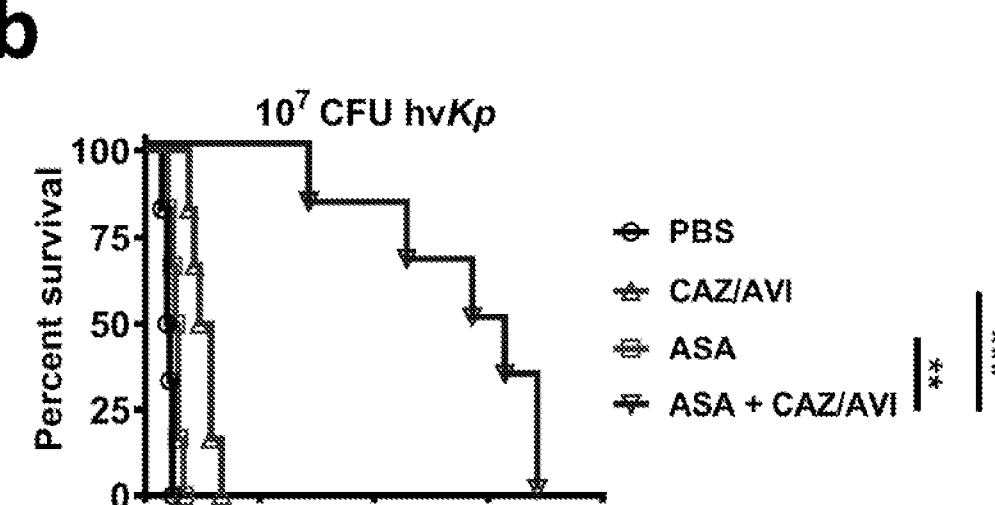
c
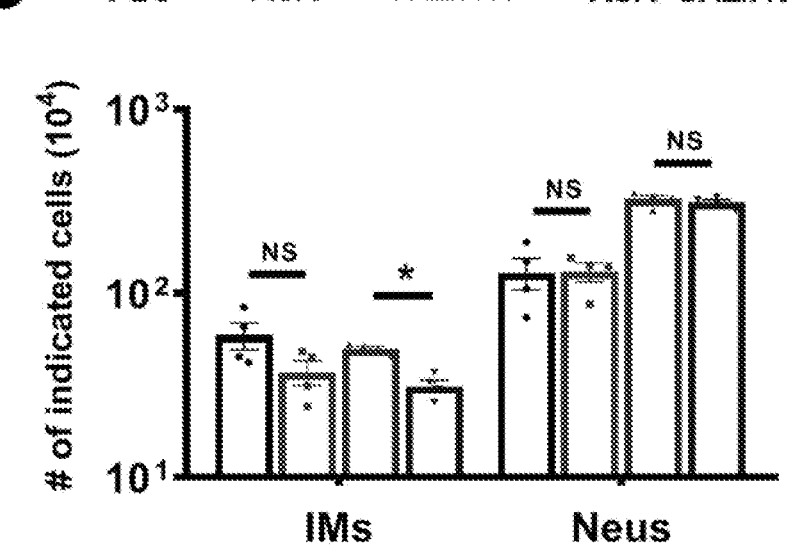
FIG. 6 (Continued)

Phenotypic and genotypic characteristics of *K. pneumoniae* strains tested in this study.

| Strain ID | MLST Type | Serotypes | Virulence genes | Resistance determinants | MIC values (µg mL⁻¹) | | | | | | | |
|---|---|---|---|---|---|---|---|---|---|---|---|---|
| | | | | | IMP | AMK | CIP | CTX | CAZ | MRP | PB | TIG |
| 17ZR101 | ST86 | K2 | *irp1*; *irp2*; *iucABCDiutA*; *iroBCDN*; *kvgA*; *kvgS*; *qnrs1*; *mrkABCDFHIJ*; *rmpA* | *amp(H)*; *blaKPC-2*; *blaSHV-106*; *oqxAB*. | 32 | 1 | 1 | >128 | >128 | >128 | 4 | 1 |
| HKU1 | ST718 | K9 | *mrkABCDFHIJ* | *aac (3)-IIa*, *blaCTX-M-3*; *blaSHV-26*, *blaTEM-1B*; *dfrA26*, *floR2*; *fosA5*; *mph(A)t*; *oqxAB*; *qnrB2t*; *sttA4*; *srrB1*; *sul1*; *sul2*; *tet(A)* | 0.5 | 4 | 8 | >128 | 64 | 32 | 4 | 2 |

IPM, imipenem; AMK, amikacin; CIP, ciprofloxacin; CTX, cefotaxime; CAZ, ceftazidime; MRP, meropenem; PB, polymyxin B; TIG, tigecycline

FIG. 7

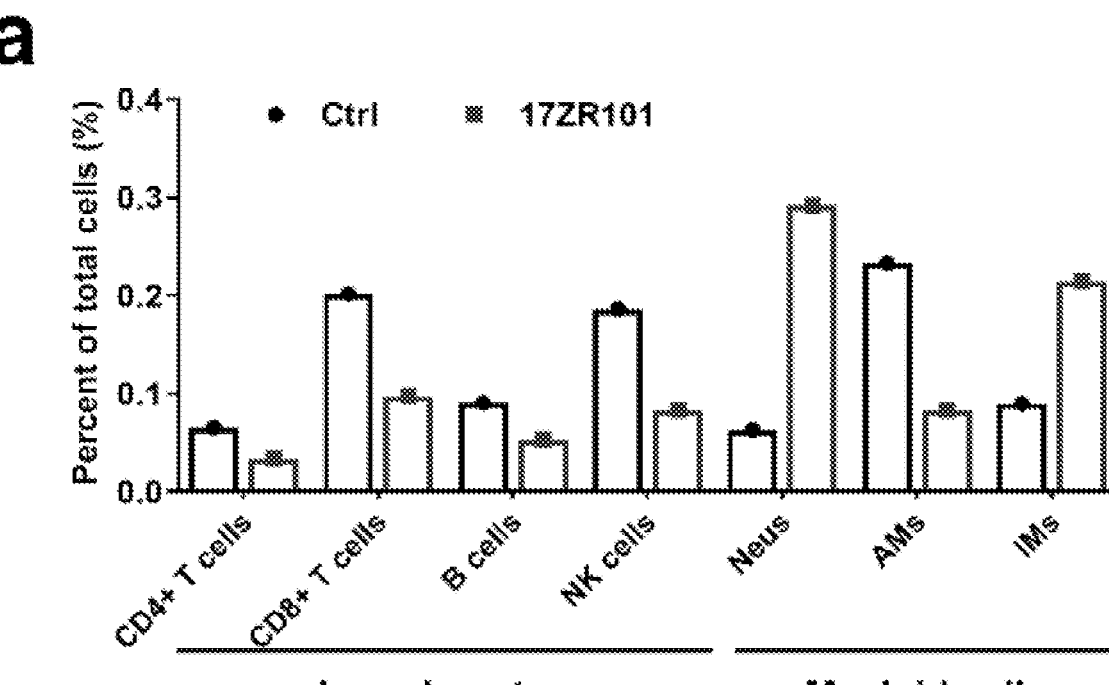
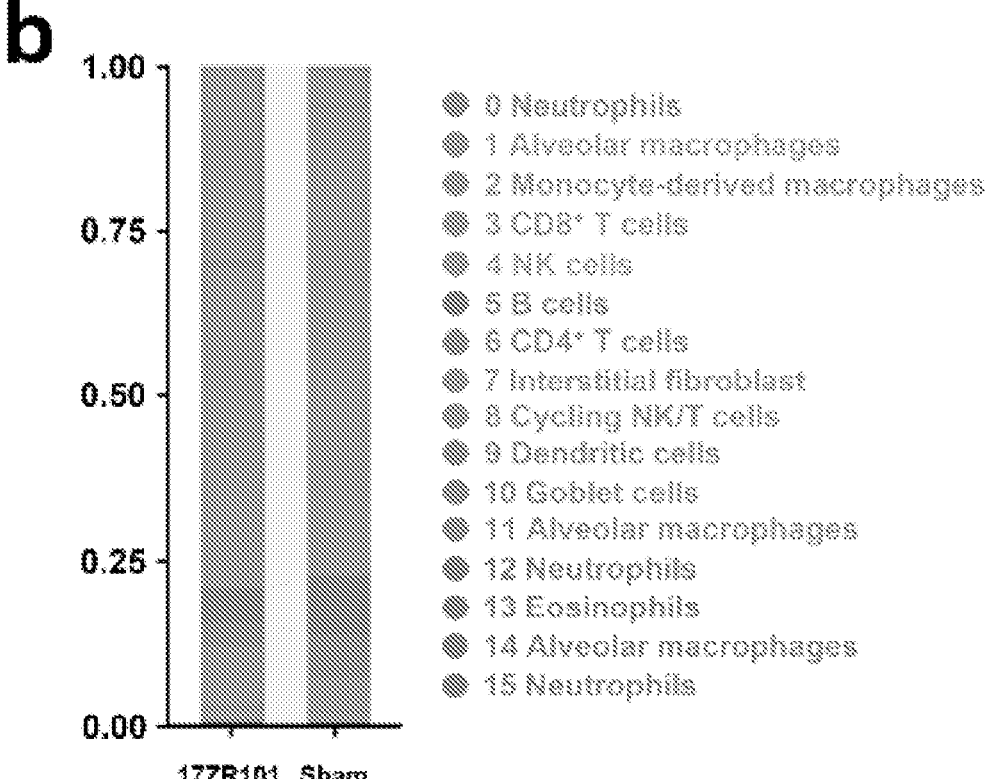
FIG. 9

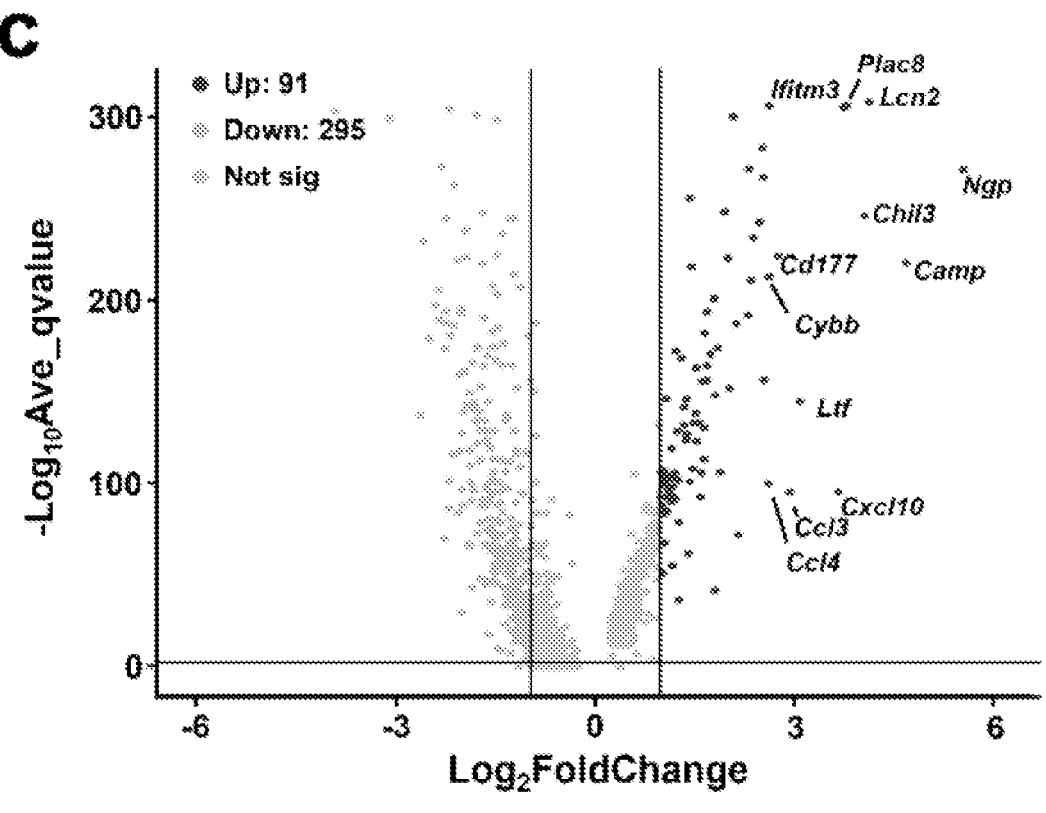
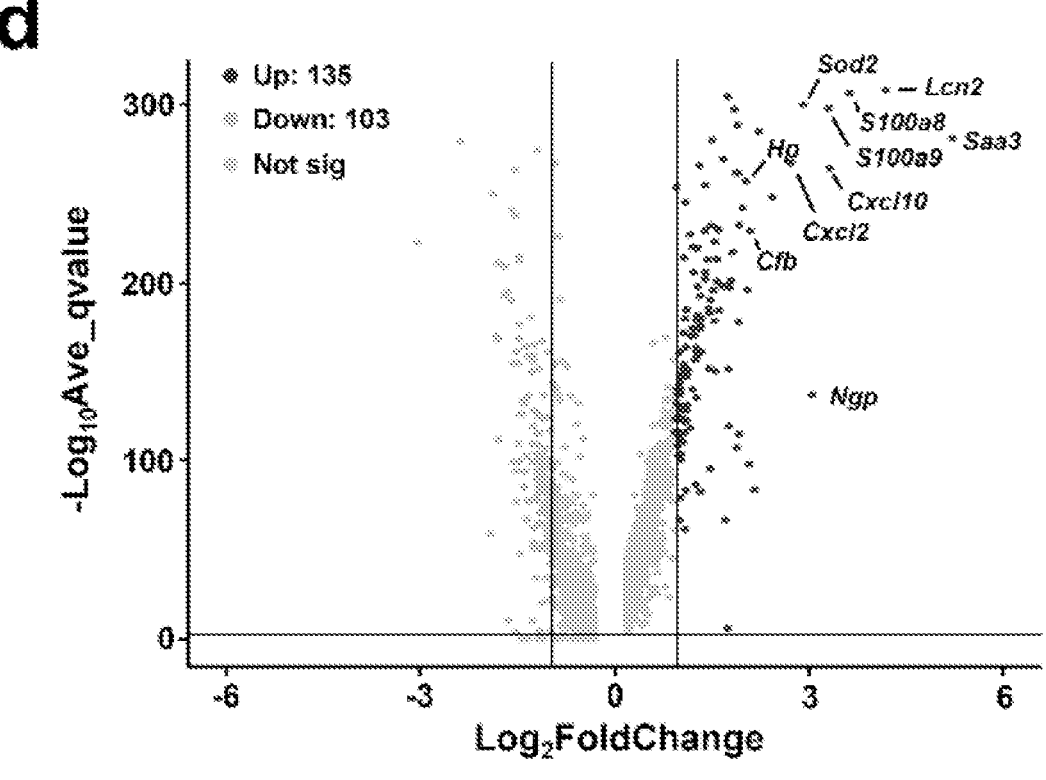
FIG. 9 (Continued)

a
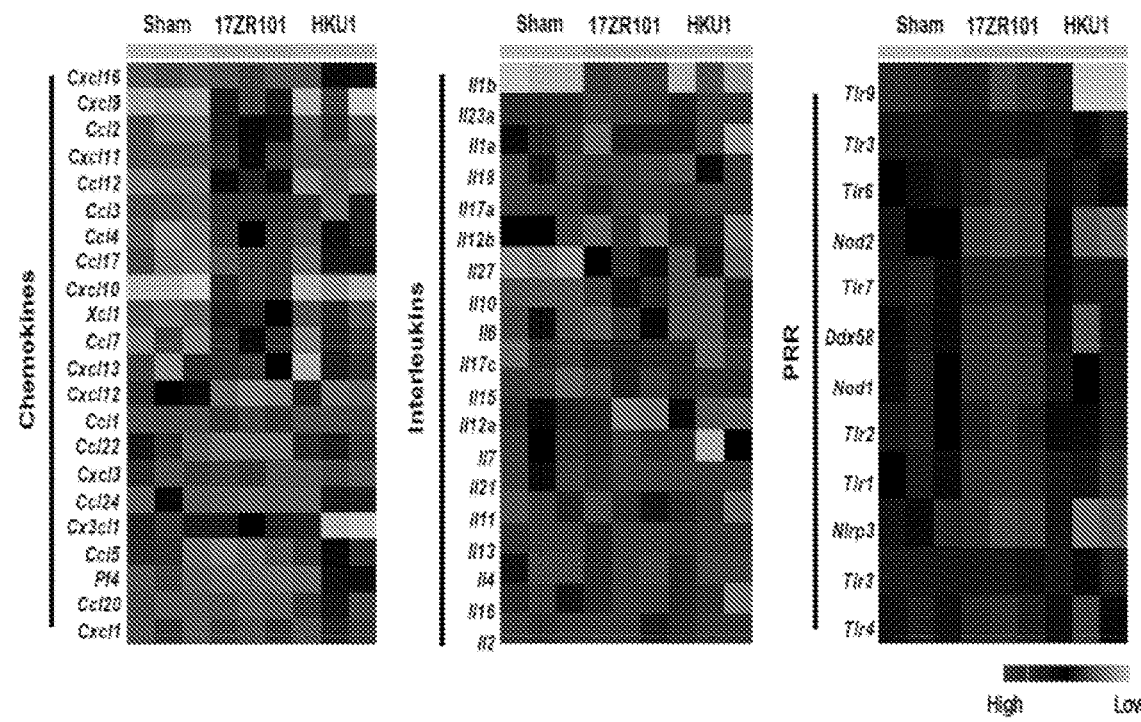
b
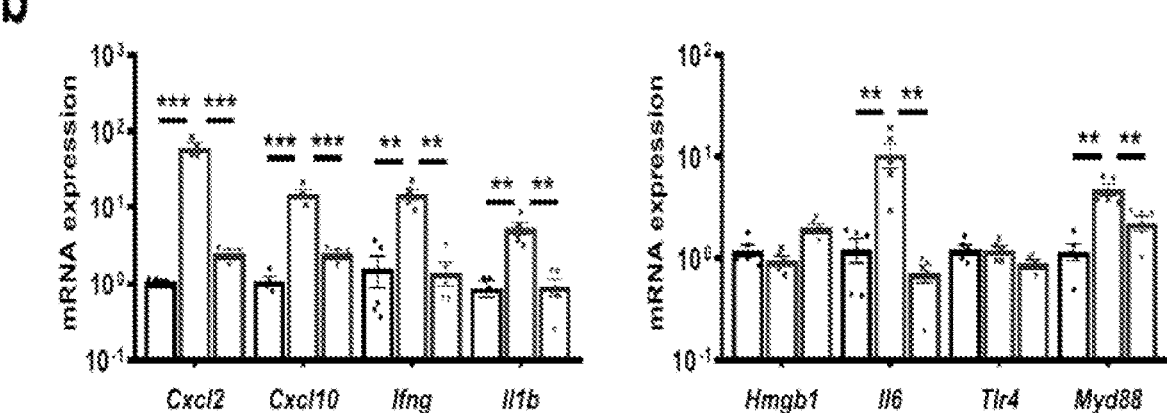
FIG. 11 a

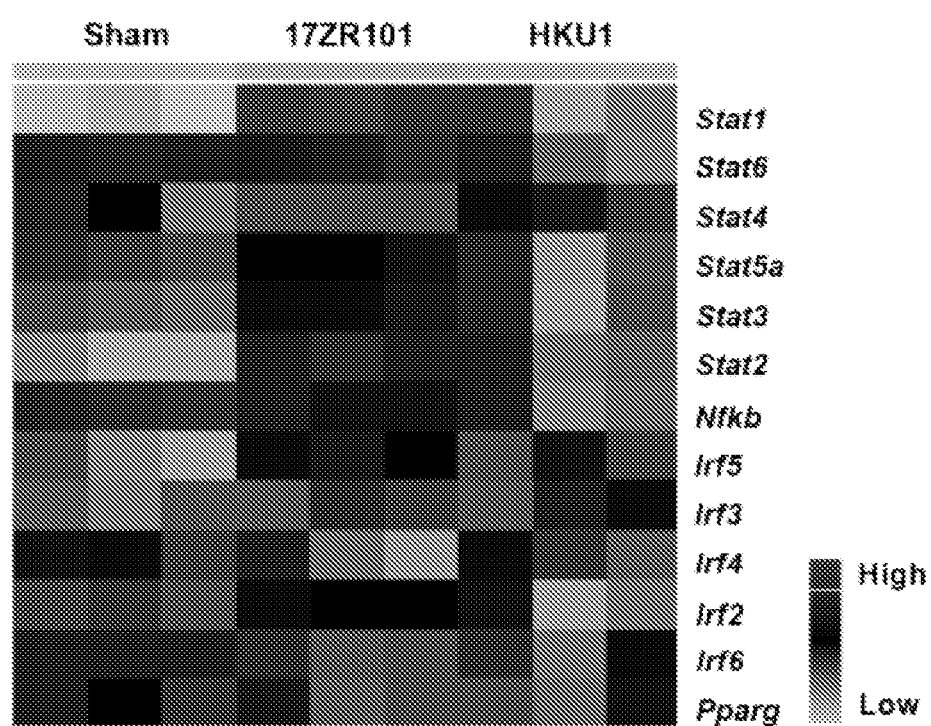
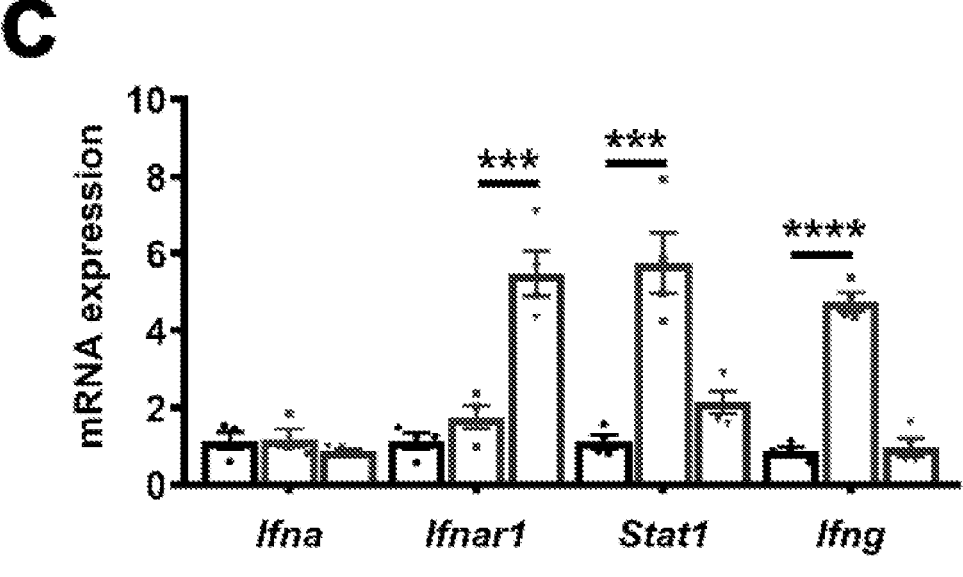
FIG. 12 (Continued)

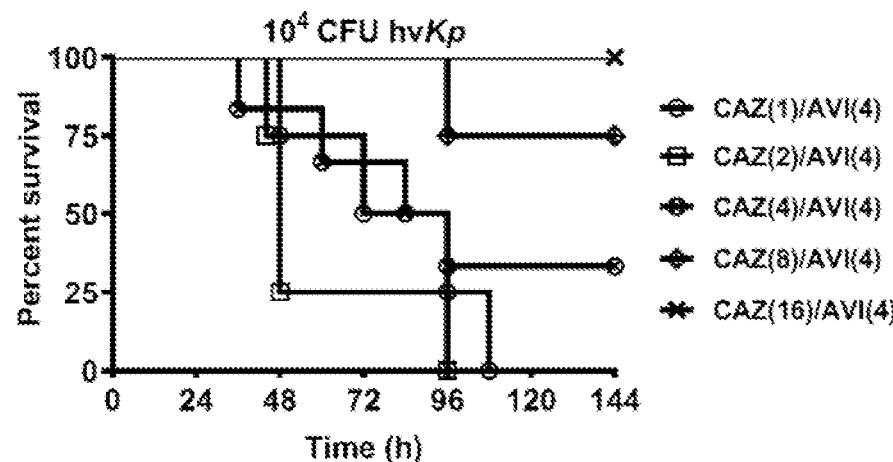
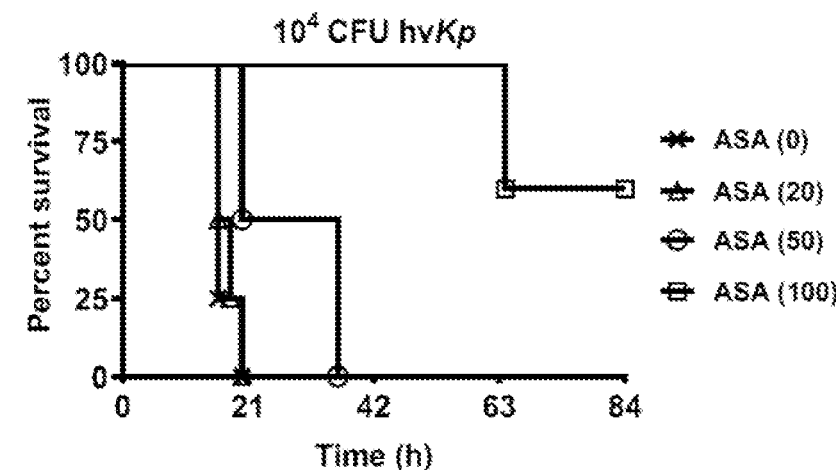
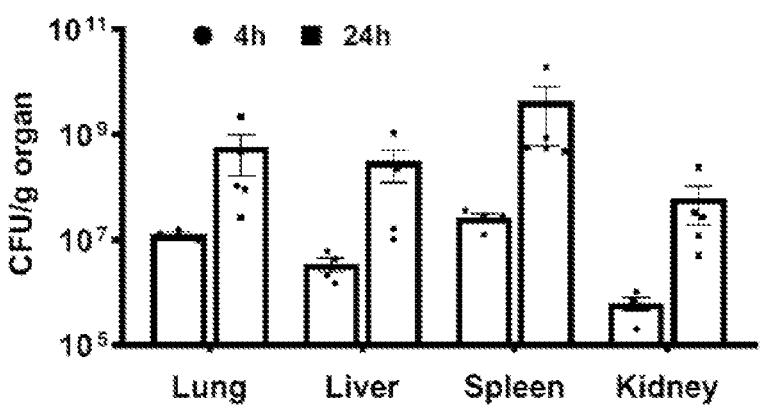
FIG. 13

METHODS FOR TREATING HYPERVIRULENT *KLEBSIELLA PNEUMONIAE* INFECTION

TECHNICAL FIELD

The present disclosure relates to methods for treating hypervirulent *Klebsiella pneumoniae* infections in a subject.

BACKGROUND

*Klebsiella pneumoniae* (Kp) is a Gram-negative commensal and opportunistic bacterium of the Enterobacteriaceae family. Certain Kp strains have acquired exogenous antibiotic resistance genes or virulence genes and have become multidrug-resistant. An notable example is the carbapenem-resistant Kp (CR-Kp) strains that cause a wide range of infections such as urinary tract infection, pneumonia, bloodstream infection, and pneumonic sepsis, primarily among the elderly, immunocompromised, critically ill and cancer patients. Hypervirulent Kp (hvKp) is currently the most common pathotype that can be differentiated from classic Kp (cKp) due to carriage of a cluster of virulence factors located in a virulence plasmid or other mobile genetic elements that can be integrated into the chromosome. The threat posed by these strains has been compounded by the fact that they undergo evolution continuously, rendering them resistant to carbapenems and various other antibiotics. Evidence gathered in our laboratory and others showed that emergence of carbapenem-resistant hvKp (CR-hvKp) was due to acquisition of a pLVPK-like virulence plasmid by the carbapenem resistant strains, or plasmids containing various carbapenemase genes such as $bla_{KPC-2}$, $bla_{VIM}$, or $bla_{NDM-1}$ harbored by the hvKp strains. Therapeutic options for infections caused by CR-hvKp, which simultaneously exhibit multidrug resistance and hypervirulence, are extremely limited, resulting in extremely high mortality among the infected patients.

In the current scenario of rapidly emerging phenotypic antimicrobial resistance in Kp, the need to hunt for novel antibiotics is urgent, so are new therapies for infections caused by the hvKp strains. For instance, phage therapy was found to exhibit promising therapeutic potential in managing Kp infection. Drug combination therapies, such as usage of econazole in combination with colistin, or the polymyxin B and zidovudine combination, was shown to be successful in treatment of Kp infection. An ideal treatment protocol should address the immune responses elicited by Kp infection. Comprehensive understanding of hvKp-host interaction, especially the hvKp-mediated immune responses, is necessary. Although Kp-host interaction has been studied for more than 20 years, most research showed that pro-inflammatory signaling was crucial to Kp clearance in the host, without providing evidence to explain why hvKp causes a high rate of death.

There thus exists a need to develop improved methods of treating hvKp infections in a subject in need thereof.

SUMMARY

The results presented herein demonstrate that hvKp-induced a type of immune response strikingly different from that induced by cKp in a mouse sepsis model, especially the reactions elicited in monocyte-derived macrophages (MDMs) and neutrophils. Notably, we it was found that hvKp induced expression of a signal transducer and activator of transcription 1 (STAT1)-dependent cytokine storm, which can be suppressed by STAT1 inhibitors or acetylsalicylic acid (ASA). Significantly, combination of antibiotic and ASA could protect mice from death, providing a therapeutic strategy for acute hvKp infection. These findings indicate that hvKp infection can be readily treated by suppressing specific host immune responses, drastically reducing the mortality rate of patients infected by hvKp.

In a first aspect, provided herein is a method of treating a hypervirulent *Klebsiella pneumoniae* (hvKp) infection in a subject in need thereof, the method comprising co-administering a therapeutically effective amount of an antibiotic and a non-steroidal anti-inflammatory drug (NSAID) or a signal transducer and activator of transcription 1 (STAT1) inhibitor to the subject.

In certain embodiments, the hvKp comprises a pLVPK-like virulence plasmid or a pK2044-like virulence plasmid.

In certain embodiments, the hvKp comprises one or more carbapenemase genes selected from the group consisting of $bla_{KPC-2}$, $bla_{VIM}$, $bla_{IMP}$, $bla_{OXA-48}$, $bla_{VIM}$, $bla_{SPM}$, $bla_{AIM}$, $bla_{DIM}$, $bla_{GIM}$, $bla_{SIM}$, and $bla_{NDM-1}$.

In certain embodiments, the hvKp comprises one or more carbapenemase genes selected from the group consisting of $bla_{KPC-2}$, $bla_{VIM}$, $bla_{IMP}$, $bla_{OXA-48}$, $bla_{VIM}$, $bla_{SPM}$, $bla_{AIM}$, $bla_{DIM}$, $bla_{GIM}$, $bla_{SIM}$, and $bla_{NDM-1}$.

In certain embodiments, the hvKp infection causes increased expression in the subject of one or more genes selected from the group consisting of Nlrp3, Caspase-1, Caspase-11, Gsdmd, and Il1b.

In certain embodiments, the NSAID is acetylsalicylic acid, naproxen, or a pharmaceutically acceptable salt thereof.

In certain embodiments, the STAT1 inhibitor is epigallocatechin-3 gallate, nifuroxazide, fludarabine, or a pharmaceutically acceptable salt thereof.

In certain embodiments, the antibiotic is an aminoglycoside, a cephalosporin, a quinolone, or a carbapenem.

In certain embodiments, the antibiotic is cefotaxime, cefpodoxime, ceftizoxime, ceftriaxone, ceftazidime, cefoperazone, cefepime, cefozopran, cefpirome, cefquinome, ceftobiprole, ceftaroline, ceftolozane, or a pharmaceutically acceptable salt thereof.

In certain embodiments, the method further comprises the step of co-administering a β-lactamase inhibitor.

In certain embodiments, the β-lactamase inhibitor is sulbactam, tebipenem, clavulanic acid, tazobactam, avibactam, relebactam, vaborbactam, or a pharmaceutically acceptable salt thereof.

In certain embodiments, the NSAID is acetylsalicylic acid or a pharmaceutically acceptable salt thereof and the antibiotic is a cephalosporin.

In certain embodiments, the method further comprises the step of co-administering a β-lactamase inhibitor.

In certain embodiments, the hvKp comprises one or more of a pLVPK-like virulence plasmid and a carbapenemase genes selected from the group consisting of $bla_{KPC-2}$, $bla_{VIM}$, $bla^{IMP}$, $bla_{OXA-48}$, $bla_{VIM}$, $bla_{SPM}$, $bla_{AIM}$, $bla_{DIM}$, $bla_{GIM}$, $bla_{SIM}$, and $bla_{NDM-1}$; the NSAID is acetylsalicylic acid or a pharmaceutically acceptable salt thereof; the antibiotic is ceftazidime; and the method further comprises co-administering avibactam or a pharmaceutically acceptable salt thereof.

In certain embodiments, the method further comprises the step of providing a sample comprising the hvKp or suspected of comprising the hvKp from the subject; and determining whether the hvKp comprises one or more of a pLVPK-like virulence plasmid and a carbapenemase genes selected from the group consisting of $bla_{KPC-2}$, $bla_{VIM}$ bla$_{IMP}$, bla$_{OXA-48}$, bla$_{VIM}$, bla$_{SPM}$, bla$_{AIM}$, bla$_{DIM}$, bla$_{GIM}$, bla$_{SIM}$, and bla$_{NDM-1}$ prior to the step of co-administering a therapeutically effective amount of the antibiotic and the non-steroidal anti-inflammatory drug (NSAID) or the STAT1 inhibitor to the subject.

BRIEF DESCRIPTION OF THE DRAWINGS

The above and other objects and features of the present disclosure will become apparent from the following description of the disclosure, when taken in conjunction with the accompanying drawings.

FIG. 7 depicts a table showing the phenotypic and genotypic characteristics of *K. pneumoniae* strains tested in this study.

FIG. 11 depicts experimental results showing RT-qPCR confirmed RNA-Seq data. (a) Heatmap of gene clusters of DEGs in lung cells of Sham-, 17ZR101- and HKU1-infected mice. (b) Fold-change in genes of the M1 markers, proinflammatory cytokines in lung cells which exhibited altered gene expression patterns in qPCR analysis of 17ZR101-treated mice, with Sham- and HKU1-treated lung cells being the control (n=5 per group).

FIG. 13 depicts experimental results showing (a) C57BL6 mice were inoculated with $10^4$ CFU hvKp strain and treated with indicated dose of CAZ and fixed dose of AVI at 3 hpi. The survival curve was recorded. (b) Survival curve of mice challenged by ~$10^4$ CFU 17ZR101 with ASA administration at 3 hpi. (c) C57BL6 mice were inoculated with $10^7$ CFU of indicated hvKp strain 17ZR101 and treated with CAZ/AVI+ASA at 1 hpi. Bacteria burdens of infected mice at 4 and 24 hpi were recorded.

DETAILED DESCRIPTION

Definitions

Figure 1:
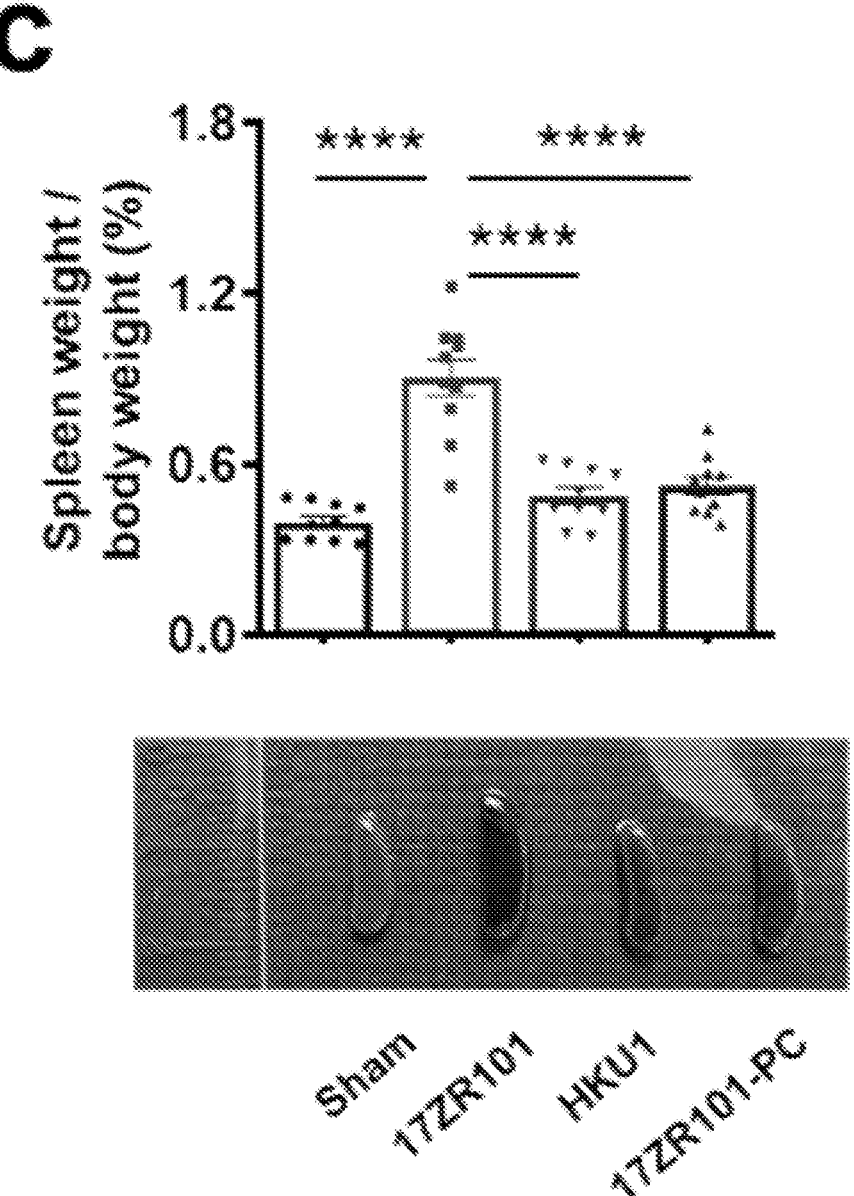
FIG. 1 depicts data demonstrating HvKp resists killing by immune cells in a mouse sepsis model. (a) C57BL6 mice were inoculated with $10^4$ CFU of indicated Kp strains and the Kaplan-Meier survival curve was recorded. n=10. (b) Percentage of body weight loss of Kp-infected mice at 12 hpi, n=10. (c) Spleen weight and representative image of spleens harvested from Kp-infected mice. Bacterial load in various organs of mice at 6 (d) and 12 (e) hpi. n=5. (f) Cell suspensions recovered from lungs and spleens of the test mice were incubated with 300 µg/mL Amikacin for 1 h and the number of CFU was counted. n=5. *p<0.05, p<0.01, **p<0.0001.
Figure 1:
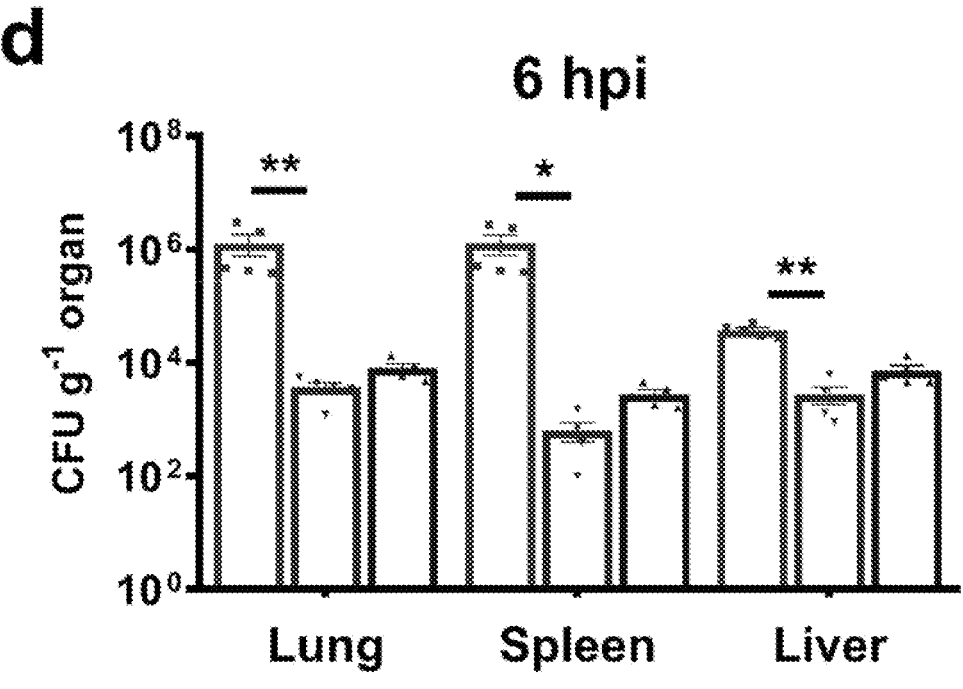

The terms used in this application are well known in the art and have the following meanings:

As used herein, the term "subject" refers to an animal. In certain aspects, the animal is a mammal. For example, primates, cows, sheep, goats, horses, dogs, cats, rabbits, rats, mice, and the like. In certain embodiments, the subject is a human.

As used herein, the terms "co-administration" and "co-administering" refer to both concurrent administration (administration of two or more therapeutic agents at the same time) and time varied administration (administration of one or more therapeutic agents at a time different from that of the administration of an additional therapeutic agent or agents). In certain embodiments, the therapeutic agents are present in the patient to some extent at the same time.

As used herein, the term "inhibit", "inhibition" or "inhibiting" refers to the reduction or suppression of a given condition, symptom, or disorder, or disease, or a significant decrease in the baseline activity of a biological activity or process, or a diminishment in the viability, number or growth speed of the flora/microflora.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In certain embodiments, "treat", "treating" or "treatment" refers to alleviating or ameliorating at least one physical parameter including those which may not be discernible by the patient. In yet other embodiments, "treat", "treating" or "treatment" refers to modulating the disease or disorder, either physically, (e.g., stabilization of a discernible symptom), physiologically, (e.g., stabilization of a physical parameter), or both. In yet other embodiments, "treat", "treating" or "treatment" refers to preventing or delaying the onset or development or progression of the disease or disorder.

The term "therapeutically effective amount" as used herein, means that amount of the compound or pharmaceutical agent that elicits a biological and/or medicinal response in a cell culture, tissue system, subject, animal, or human that is being sought by a researcher, veterinarian, clinician, or physician, which includes alleviation of the symptoms of the disease, condition, or disorder being treated.

As used herein, the term "combinational use" includes treatment regimens in which each drug does not have to be administered by the same route of administration or at the same time. Fixed combination products are also within the scope of the invention. The administration of a pharmaceutical combination product described herein results in a beneficial effect, e.g., a synergistic therapeutic effect, compared to a monopharmacotherapy applying only one of its pharmaceutically active ingredients.

As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In certain embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable salts derived from appropriate bases include alkali metal, alkaline earth metal, ammonium and $N^+(C_1-C_4 \text{ alkyl})_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, non-toxic ammonium, quaternary ammonium, and amine cations formed using counterions, such as halide, hydroxide, carboxylate, sulfate, phosphate, nitrate, lower alkyl sulfonate, and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In certain embodiments, the pharmaceutically acceptable base addition salt is chosen from ammonium, potassium, sodium, calcium, and magnesium salts.

As used herein, the term "β-lactamase inhibitor" means a compound having the ability to at least partially or fully inhibit the activity of one or more β-lactamase enzymes.

Abbreviations

AMs: Alveolar macrophages; ASA: acetylsalicylic acid; AVI: avibactam; CAZ: ceftazidime; CFU: colony-forming unit; CR-hvKp: carbapenem-resistant hvKp; CR-Kp: carbapenem-resistant Kp; hpi: hour post-infection; hvKp: hypervirulent Kp; IFN-γ: interferon-γ; IL-6: interleukin-6; IRFs: interferon-regulatory factors; Kp: *Klebsiella pneumoniae*; IMs: interstitial macrophages; Neus: neutrophils; NK: natural killer; NSAIDs: non-steroidal anti-inflammatory drugs; RNA-seq: RNA sequencing; STAT1: signal transducer and activator of transcription 1.

The present disclosure provides a method of treating a hvKp infection in a subject in need thereof, the method comprising co-administering a therapeutically effective amount of an antibiotic and a NSAID or a STAT1 inhibitor to the subject.

The hvKp can comprises a pLVPK-like virulence plasmid and/or one or more carbapenemase genes selected from the group consisting of $bla_{KPC-2}$, $bla_{VIM}$, $bla_{IMP}$, $bla_{OXA-48}$, $bla_{VIM}$, $bla_{SPM}$, $bla_{AIM}$, $bla_{DIM}$, $bla_{GIM}$, $bla_{SIM}$, and $bla_{NDM-1}$. In certain embodiments, hvKp strain 17ZR101 harbors a pLVPK-like virulence plasmid and carbapenemase gene $bla_{KPC-2}$.

The hvKp infection can result in increased expression in the subject of one or more genes selected from the group consisting of Nlrp3, Caspase-1, Caspase-11, Gsdmd, and Il1b.

The NSAID can be paracetamol, acetaminosalol, ASA (aspirin), aminoprofen, amfenac, aminoantipyrine, ampiroxicam, anileridine, bermoprofen, α-bisabolol, bromfenac, bromosaligenin, butibufen, carprofen, celecoxib, cromoglycate, cinmetacin, clidanac, clopirac, dexibuprofen, diclofenac sodium, diflunisal, drogelon, enfenamic acid, etofenamate, felbinac, fenbufen, fenclozic acid, fendosal, fenoprofen, fentiazac, fepradinol, flufenac, flufenamic acid, flunixin, flunoxaprofen, flurbiprofen, oxyphenonii bromidum, spirosal, ibufenac, ibuprofen, ibuproxam, indomethacin, indoprofen, Isofezolac, isoxepac, isoxicam, ketoprofen, ketorolac, lornoxicam, loxoprofen, meclofenamic acid, mefenamic acid, meloxicam, mesalazine, metiazinic acid, oxaprozin, singulair, nabumetone, sodium naproxen, niflumic acid, nimesulide, paracetamol, parsalmide, perisoxal, phenylacetyl salicylate, phenylbutazone, salol, pirazolac, piroxicam, pirprofen, protizinic acid, trans-resveratrol, salacetamide, salicylic amide, salicylic amide-O-acetate, salicylsulfuric acid, saligenin, salicylic amide, salsalate, sulindac, sutoprofen, suxibuzone, tamoxifen, tenoxicam, tiaprofenic acid, tiaramide, ticlopidine, tinoridine, tolfenamic acid, tolmetin, zaltoprofen, zomepirac, tomoxiprole, zafirlukast, or a pharmaceutically acceptable salt thereof. In certain embodiments, the NSAID is acetylsalicylic acid or a pharmaceutically acceptable salt thereof.

In certain embodiments, the STAT1 inhibitor is a small molecule, antibody, protein, interfering nucleic acid, or the like. Exemplary STAT1 inhibitors, include, but are not limited to epigallocatechin-3 gallate, nifuroxazide, fludarabine, or a pharmaceutically acceptable salt thereof.

The antibiotic can be an aminoglycoside, a cephalosporin, a quinolone, or a carbapenem.

The aminoglycoside can be streptomycin, dibekacin, kanamycin, tobramycin, amikacin, arbekacin, gentamicin, sagamicin, isepamicin, sisomicin, netilmicin, neomycin, paromomycin, etimicin, astromicin, ribostamycin, micronomicin, spectinomycin, or a pharmaceutically acceptable salt thereof.

The cephalosporin can be a first-generation cephalosporin, such as cefazolin, cefalexin, and cefadroxil; a second-generation cephalosporin, such as cefamandole, cefoxitin, cefaclor, cefuroxime, loracarbef, and cefotetan; a third-generation cephalosporin, such as cefotaxime, cefpodoxime, ceftizoxime, ceftriaxone, ceftazidime, and cefoperazone; a fourth-generation cephalosporin, such as cefepime, cefozopran, cefpirome, and cefquinome; or a fifth-generation cephalosporin, such as ceftobiprole, ceftaroline, and ceftolozane; or a pharmaceutically acceptable salt thereof.

If the antibiotic is a cephalosporin or other β-lactam antibiotic a β-lactamase inhibitor can optionally be co-administered to enhance the action of the cephalosporin or other β-lactam. In such instances, the β-lactamase inhibitor can be selected from the group consisting of In certain embodiments, the quinolone is ciprofloxacin, garenoxacin, gatifloxacin, gemifloxacin, levofloxacin, moxifloxacin, fleroxacin, lomefloxacin, nadifloxacin, norfloxacin, ofloxacin, pefloxacin, rufloxacin, balofloxacin, grepafloxacin, pazufloxacin, sparfloxacin, temafloxacin, clinafloxacin, sitafloxacin, prulifloxacin, besifloxacin, delafloxacin, danofloxacin, difloxacin, enrofloxacin, ibafloxacin, marbofloxacin, orbifloxacin, sarafloxacin, or a pharmaceutically acceptable salt thereof.

In certain embodiments, the method further comprises the step of providing a sample comprising the hvKp or suspected of comprising the hvKp from the subject; and determining whether the hvKp comprises one or more of a pLVPK-like virulence plasmid and a carbapenemase genes selected from the group consisting of $bla_{KPC-2}$, $bla_{VIM}$, and $bla_{NDM-1}$ prior to the step of co-administering a therapeutically effective amount of the antibiotic and the non-steroidal anti-inflammatory drug (NSAID) or the STAT1 inhibitor to the subject.

The type of sample is not particularly limited and can be, for example, blood, serum, plasma, urine, stool, saliva, sputum, spinal fluid, or other body fluids, such as tissue fluid, or saliva, and swabs, or dilutions thereof.

The step of determining whether the hvKp comprises one or more of a pLVPK-like virulence plasmid and a carbapenemase genes selected from the group consisting of $bla_{KPC-2}$, $bla_{VIM}$, and $bla_{NDM-1}$ can be accomplished using any method known to those of skill in the art. In certain embodiments, the method comprises nucleic acid analysis, e.g., using restriction enzymes, hybridization, polymerase chain reaction (PCR) amplification and/or sequencing, culture-based screening for nutrient requirements and/or antimicrobial sensitivity, analyzing fatty acid distribution, and/or test antigens, or combinations thereof.

The antibiotic, NSAID or STAT1 inhibitor and optionally the β-lactamase inhibitor may be administered concurrently (e.g., simultaneously, essentially simultaneously or within the same treatment protocol) or sequentially, depending upon the nature of the hvKp infection, the condition of the subject, and the actual choice of the antibiotic, NSAID or STAT1 inhibitor, and optionally β-lactamase inhibitor to be administered in conjunction (i.e., within a single treatment protocol).

If the antibiotic, NSAID or STAT1 inhibitor and optionally the β-lactamase inhibitor are not administered simultaneously or essentially simultaneously, then the optimum order of administration of the antibiotic, NSAID or STAT1 inhibitor and optionally the β-lactamase inhibitor, may be different for different types of hvKp infections. Thus, in certain situations the antibiotic be administered first followed by the administration of the NSAID or STAT1 inhibitor and optionally the β-lactamase inhibitor; and in other situations the NSAID or STAT1 inhibitor and optionally the β-lactamase inhibitor may be administered first followed by the administration of the antibiotic. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the subject.

The mode of administration of the therapeutic agents described herein may be any suitable route that delivers the agent to the subject, such as parenteral administration, e.g., intradermal, intramuscular, intraperitoneal, intravenous or subcutaneous, pulmonary; transmucosal (oral, intranasal, intravaginal, rectal); using a formulation in a tablet, capsule, solution, suspension, powder, gel, particle; and contained in a syringe, an implanted device, osmotic pump, cartridge, micropump; or other means appreciated by the skilled artisan, as well known in the art. Site specific administration may be achieved by for example intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

HvKp Resists Host Immune Response in a Mouse Sepsis Model

Figure 8:
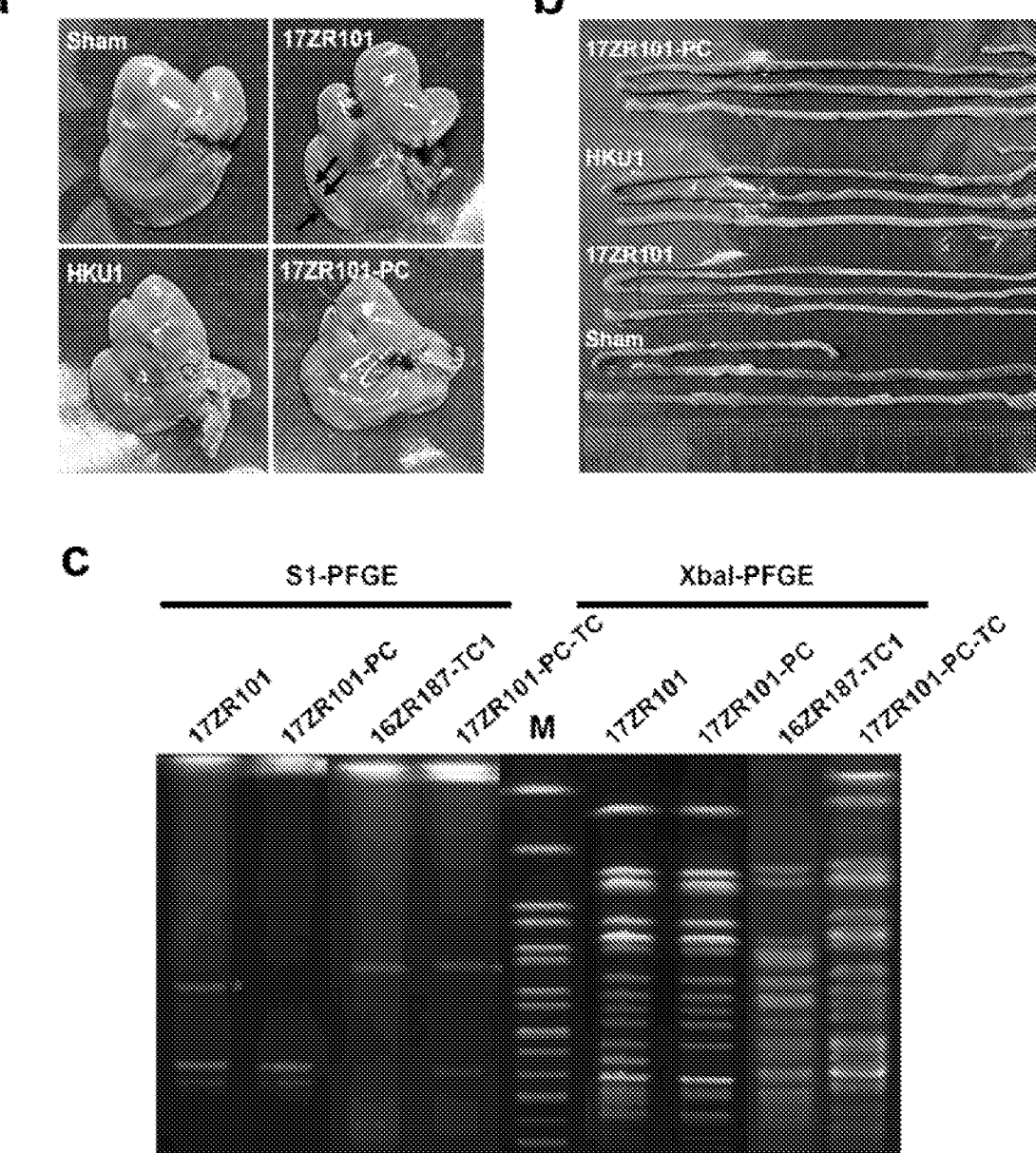
FIG. 8 depicts experimental results showing virulence plasmid curing altered the morphology of liver and small intestine in mice of hvKp infection. (a) Changes in liver morphology among mice infected by different *Klebsiella* strains. (b) HvKp infection caused thinning of the intestinal walls and production of a large amount of yellow mucus-like substance in the intestine. (c) Validation of the virulence plasmid curing and conjugation in 17ZR101 by S1- and XbaI-PFGE. "*" indicates the virulence plasmid to be cured and conjugated.

To investigate the underlying mechanisms of hvKp pathogenesis, mice were infected with 17ZR101, a K2 hvKp clinical strain, and HKU1, a clinical cKp strain, and evaluated the immunological responses elicited in the animals. Antimicrobial susceptibility tests performed on these two strains showed that they were resistant to cefotaxime, ceftazidime, and meropenem but remained susceptible to amikacin, polymyxin B and tigecycline (FIG. 7). It was found that mice infected by 17ZR101, but not HKU1 or the hvKp control strains HvKP4 and HvKP1088, lost weight and died within 24 hours post-infection (hpi) (FIG. 1a, b) This killing process was associated with a series of tissue damages and pathological changes in various organs (FIG. 1c; FIG. 8a, 8b). Moreover, 17ZR101-infection was found to result in a significantly higher bacterial burdens in blood and various organs at 6 hpi when compared with HKU1-infected animals (FIG. 1d). Consistently, 17ZR101-infected mice continued to exhibit extremely high bacterial loads at 12 hpi. In comparison, HKU1 was almost cleared (FIG. 1e). To test if 17ZR101 survived and replicated in the phagocytes, total cells from 17ZR101-infected lungs and spleens were collected and incubated with 300 μg mL$^{-1}$ amikacin to eradicate the extracellular bacteria according to the antimicrobial susceptibility of 17R101; the number of intracellular bacteria were counted and recorded subsequently. The results showed that, although 17ZR101 could readily be engulfed, this strain could survive for a long period of time within phagocytes. (FIG. 1f).

Next, studies investigating factors that enable hvKp to cause serious and life-threatening infections in human were conducted. A K2-hvKp virulence plasmid-cured strain (17ZR101-PC, FIG. 8c) was generated to evaluate the role of the virulence plasmid in eliciting the severe symptoms during infections caused by 17ZR101. The animals infected by 17ZR101-PC all survived (FIG. 1a) and the corresponding bacterial burden in various organs also decreased significantly, almost no bacteria was detected in lung and kidney at 12 hpi (FIG. 1e). Consistently, the mild symptoms, including weight loss, and tissue damage (FIG. 1b-d; FIG. 8a, b) developed in 17ZR101-PC-infected mice were similar to those infected by HKU1, which was reversed by virulence plasmid complementary strain 17ZR101-PC-TC (FIG. 8a; FIG. 8c), confirming that the virulence plasmid played a critical role in the pathogenesis of hvKp.

High-Resolution scRNA-Seq Reveals the Immune Landscape of hvKp-Infected Lungs

Figure 2:
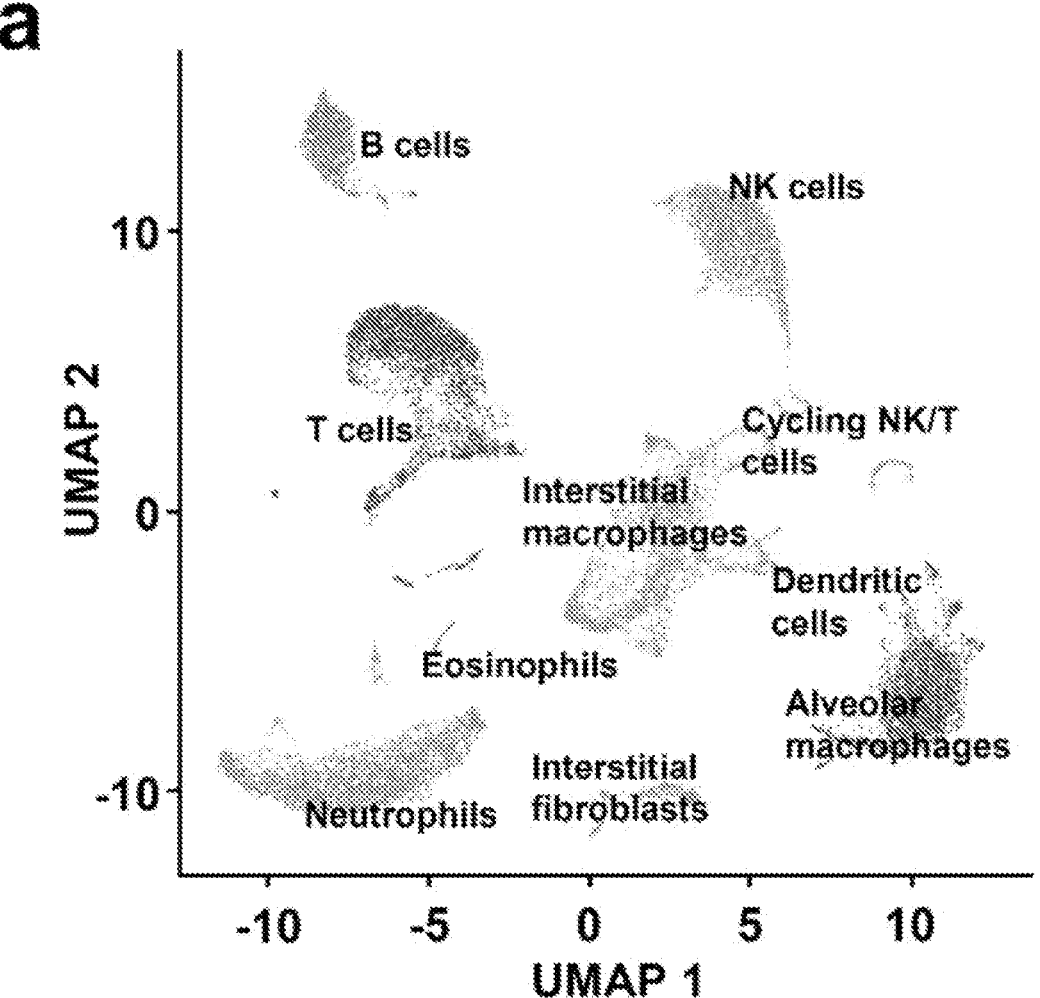
FIG. 2 depicts data showing the cellular landscape of immune cells of hvKp-infected lungs. (a) Major clusters and respective cell-type assignment in UMAP. (b) Origins of cells with same embedding as in (a). (c) Go enrichment analysis of changing pathways in MDMs and neutrophils (Neus). (d) UMAP of single cell profile coded for MDM subsets and the percentage of each subset. (e) UMAP of single cell profile coded for neutrophil subsets and the percentage of each subset.
Figure 2:
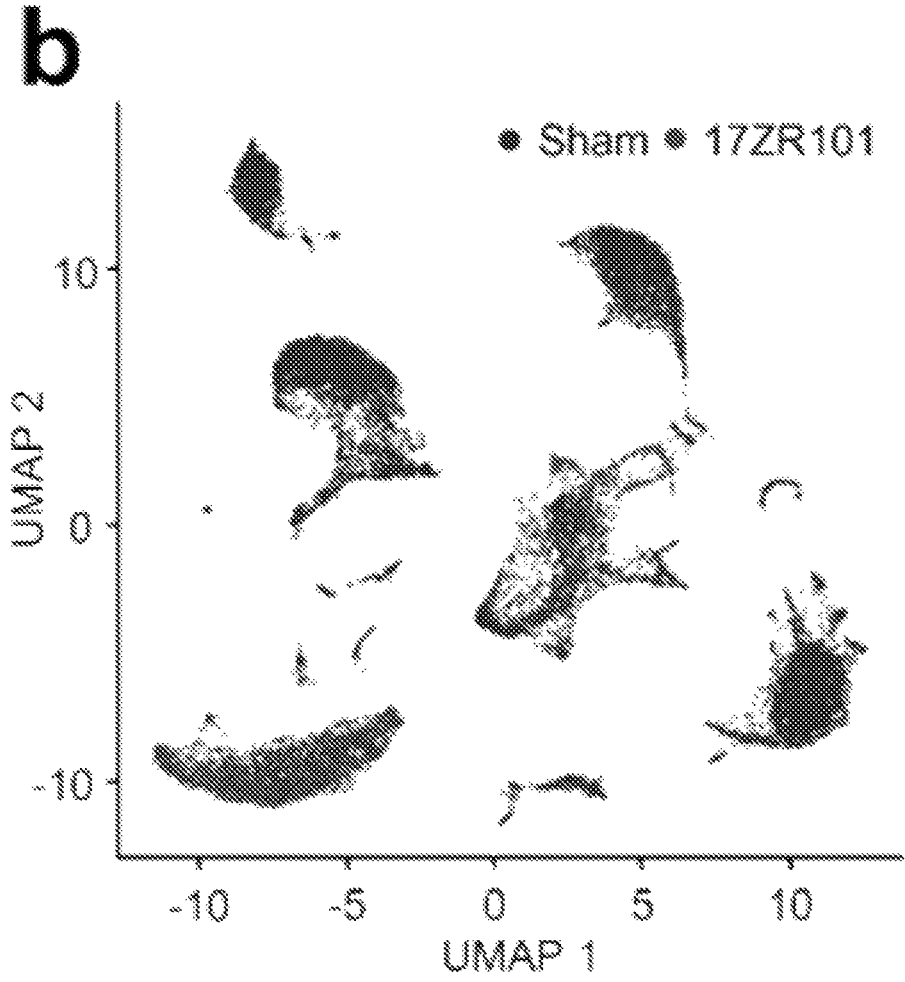
Figure 2:
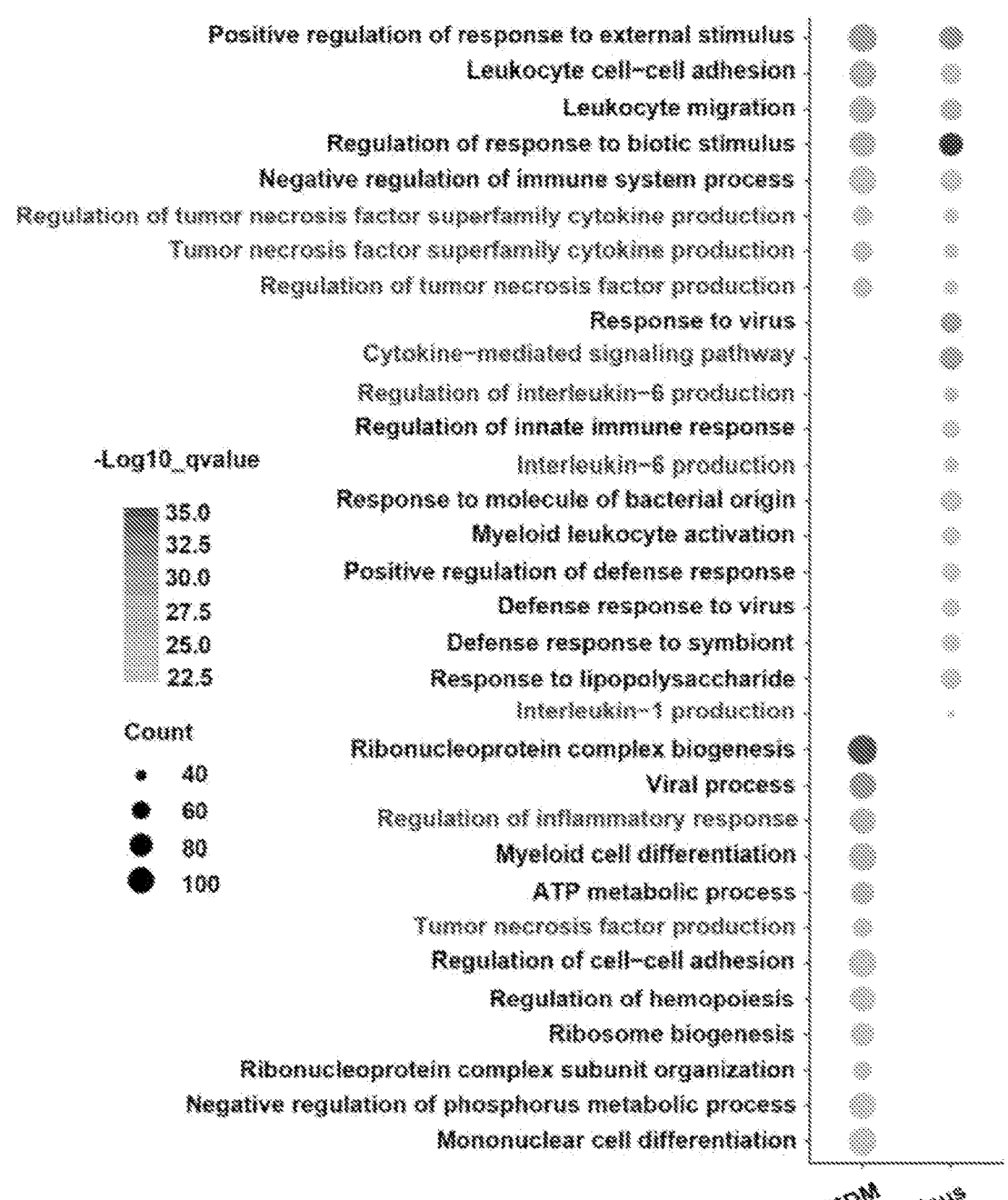
Figure 9:
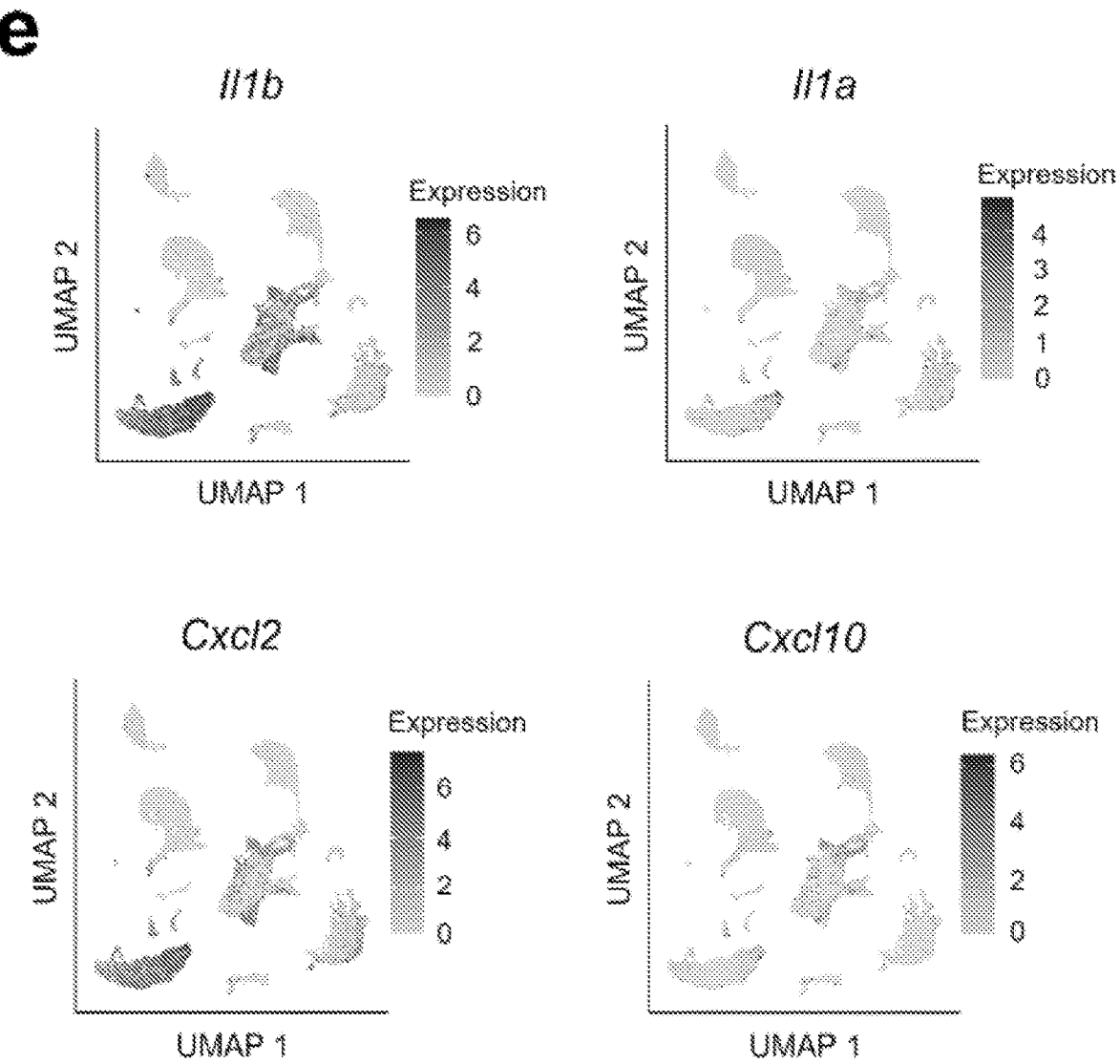
FIG. 9 depicts experimental results showing ScRNA-Seq revealed the pro-inflammatory state of IMs and Neus. (a), (b) Percentage comparison of six main type of cells (CD4$^+$ T cell, CD8$^+$ T cell, NK cell, B cell, Neutrophil, Alveolar macrophage, and monocyte-derived macrophage) identified by scRNA-Seq. Volcano plot of scRNA-Seq gene counts in Neus (c) and IMs (d) obtained from Sham- and 17ZR101-infected lungs. (e) Expression of Il1b, Il1a, Cxcl2 and Cxcl10 for the Neus and IMs.

Since strain 17ZR101 could be engulfed by phagocytes but was still able to cause severe infections in human, it was hypothesized that the symptoms of infections were actually caused by strong and over-reactive immune response of the host elicited by hvKp. To characterize the immune landscape in hvKp-infected lungs, samples of infected and sham group were collected and immediately processed to generate a single-cell suspension enriched for viable cells, and the isolated live cells were used directly. Subsequently, scRNA-seq was performed to investigate the immune heterogeneity of infected and bystander lungs. The sequencing metrics of these samples are performed by BGI. Using scRNA-seq and integrated quality control pipeline, a lung atlas that profiled 21,298 cells, including 10,489 from hvKp-infected lungs and 10,809 from sham-lungs was generated. Data was visualized with dimensionality reduction using uniform manifold approximation and projection (UMAP) (FIG. 2a, b, FIG. 9). Ten major cell types were identified: neutrophils (n=3,965 cells), alveolar macrophages (n=3,572 cells), interstitial macrophages (IMs, n=3,290 cells), T lymphocytes (n=4,297 cells), natural killer (NK) lymphocytes (n=2,896 cells), B lymphocytes (n=1,546 cells), interstitial fibroblast (n=598 cells), cycling NK/T cells (n=494 cells), dendritic cells (n=378 cells) and eosinophils (n=95 cells). Notably, 17ZR101-infection reduced the frequency of all lymphocyte compartments and AMs and increased the levels of IMs and Neus (FIG. 3b; FIG. 9a, b), indicating that IMs and Neus are the major sources of dysregulated inflammation in 17ZR101 infection.

To further unveil the role of these increased proinflammatory cells in their microenvironment, we then investigated the IMs and Neus composition and the differentially expressed genes between the Sham-treated and 17ZR101-infected groups. Among the most highly expressed genes, this signature included Lcn2 (marker of M1 polarization and neutrophil infiltration), Cd177 (a specific marker of neutrophil adhesion and transmigration), Ngp (neutrophilic granule protein), antibacterial and antiviral protein Camp and Ltf, Hp (haptoglobin, a marker of granulocyte differentiation and released by neutrophils in response to activation) and S100a8 and S100a9 in neutrophil recruitment, chemotaxis, and migration (FIG. 9c, d), indicating which was highly activated neutrophils and MDMs. IMs and Neus activation were associated with significant changes in several pathways, related to response to biotic stimulus, leukocyte migration, cytokine production, and inflammatory responses (FIG. 2c, FIG. 9e). Reclustering of IMs revealed 11 subclusters (FIG. 2d) in which 17ZR101 infection increased a M1-like subpopulation (Aif1$^+$Ctsb$^+$) and decreased a M2-like subpopulation (Fn1$^+$Thbs1$^+$), suggesting a proinflammatory state of IMs. The percentage of each cell subcluster of Neus revealed that pro-inflammatory neutrophil subset (Ngp⁺Cd177⁺) was abundant in 17ZR101-infected lungs (FIG. 2e), while a Ccl6⁺ subset was enriched in the Sham-treated samples. Altogether, these results uncover that dysregulation of cytokine production and inflammatory response are features of IMs and Neus following 17ZR101 infection.

HvKp Triggers Onset of Cytokine Storm in Mouse Upon Infection

Figure 3:
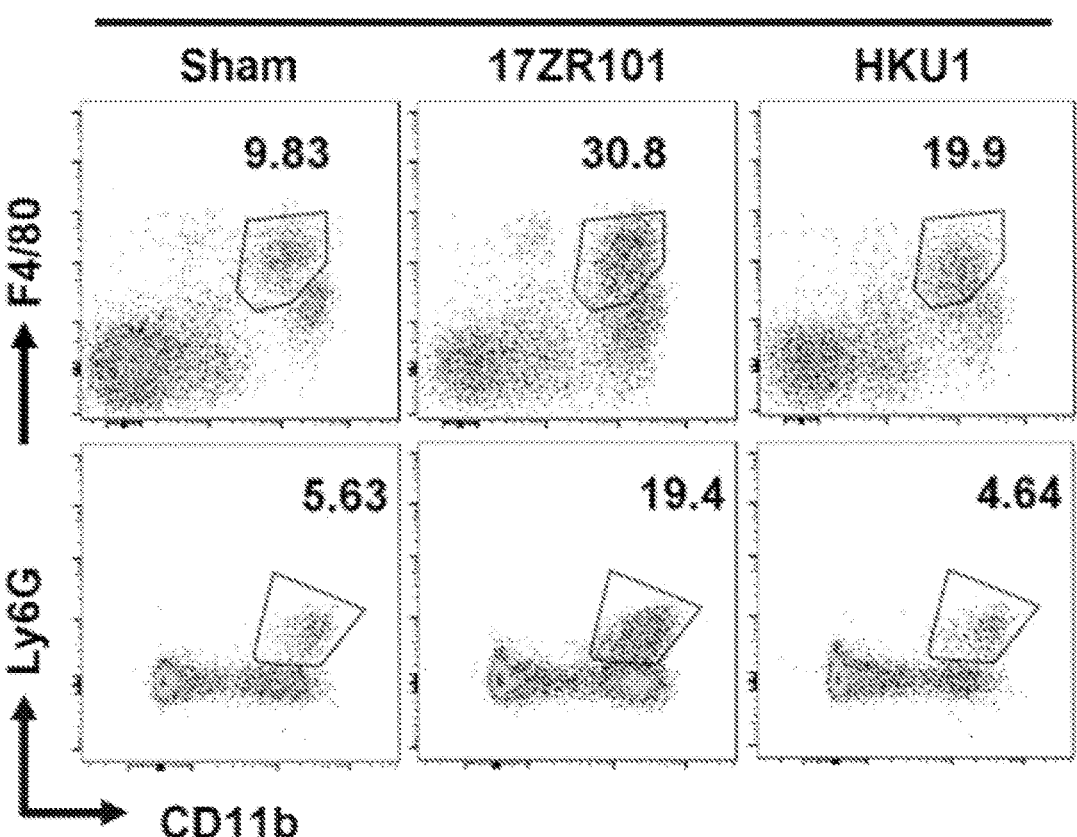
FIG. 3 depicts data demonstrating HvKp induces cytokine storm in the host. (a) C57BL6 mice were inoculated with $10^4$ CFU of indicated Kp strains and IMs and Neus cells recovered from Kp-infected lungs were analyzed by flow cytometry. n=5. (b) Quantification of IMs and Neus from (a) and Mean fluorescence intensity (MFI) of CD80 and CD206 on the surface of IMs. (c) Volcano plot of RNA-Seq gene counts in total lung cells obtained from Sham- and 17ZR101-infected mice (n=3 mice per group). (d) Enriched GO analysis showing changed pathways in 17ZR101- and HKU1-infected lung cells. (e) Heatmap depicting the differential expression patterns of the proinflammatory and neutrophil activation marker gene clusters in the Sham-, 17ZR101- and HKU1-infected groups of mice. (f) Quantification of serum IL-6, IFN-γ and IL-1β levels by ELISA. *p<0.05, p<0.01, *p<0.001, ****p<0.0001.
Figure 3:
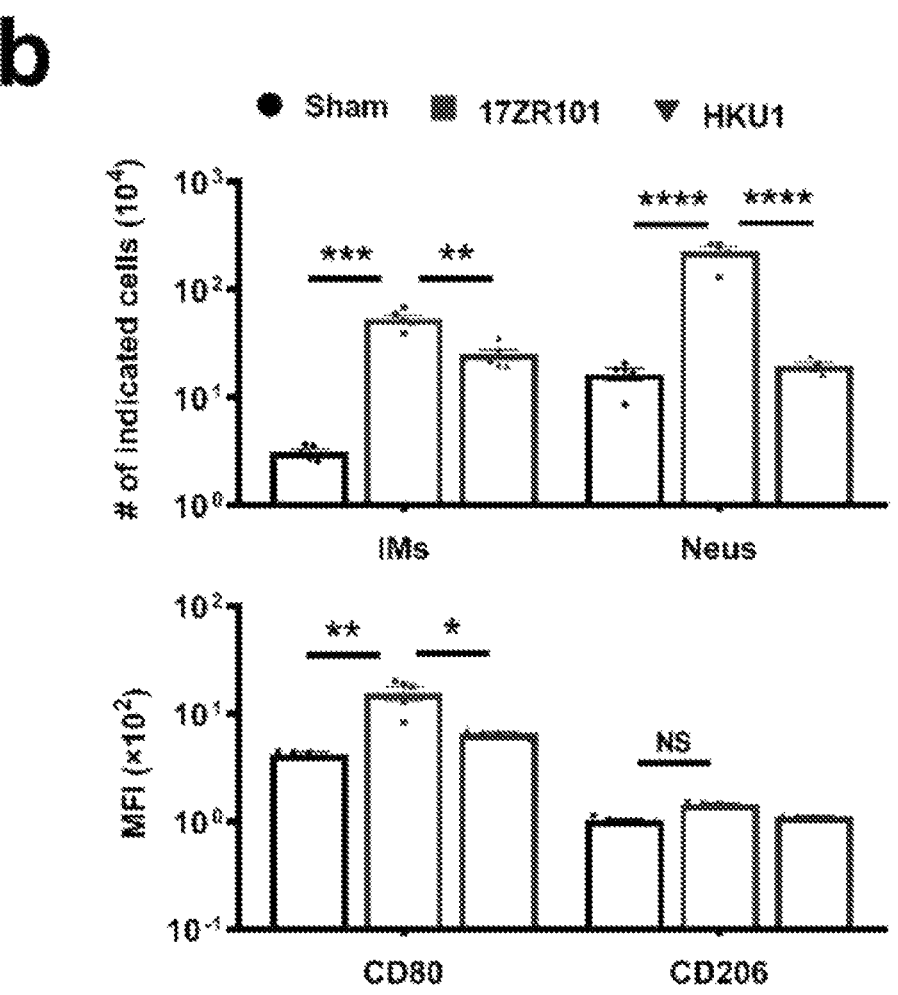
Figure 3:
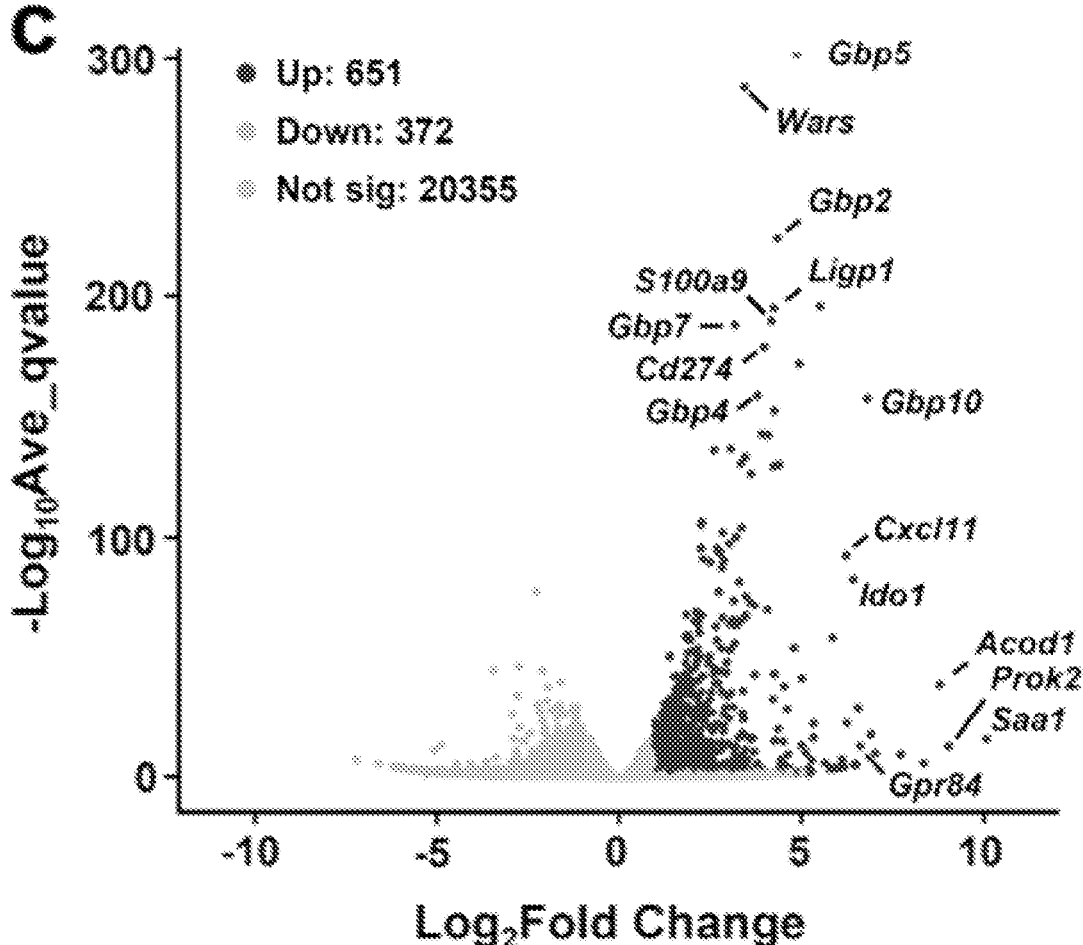
Figure 3:
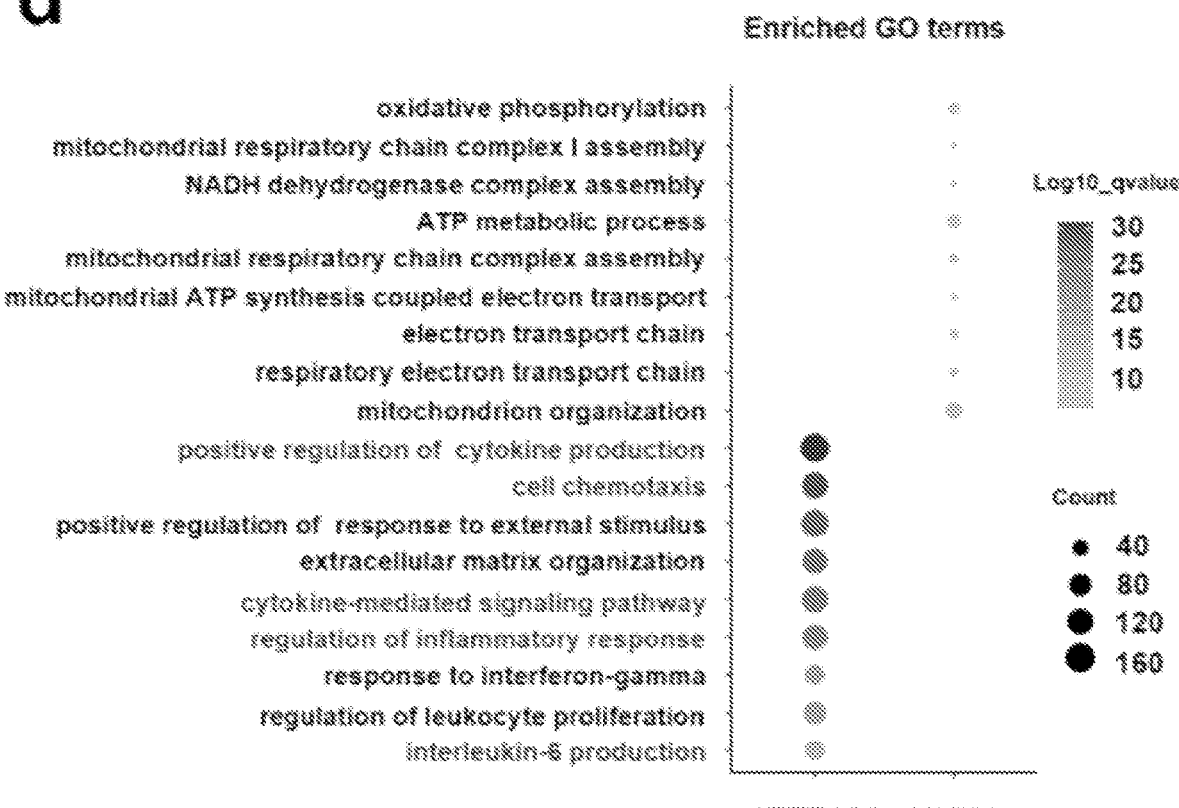
Figure 3:
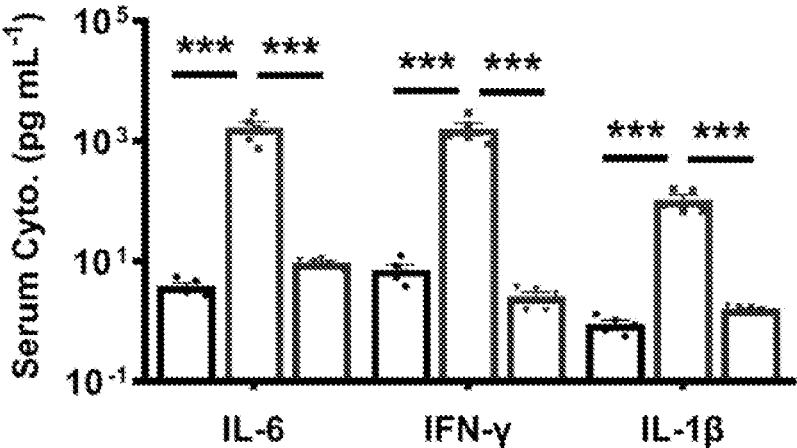
Figure 10:
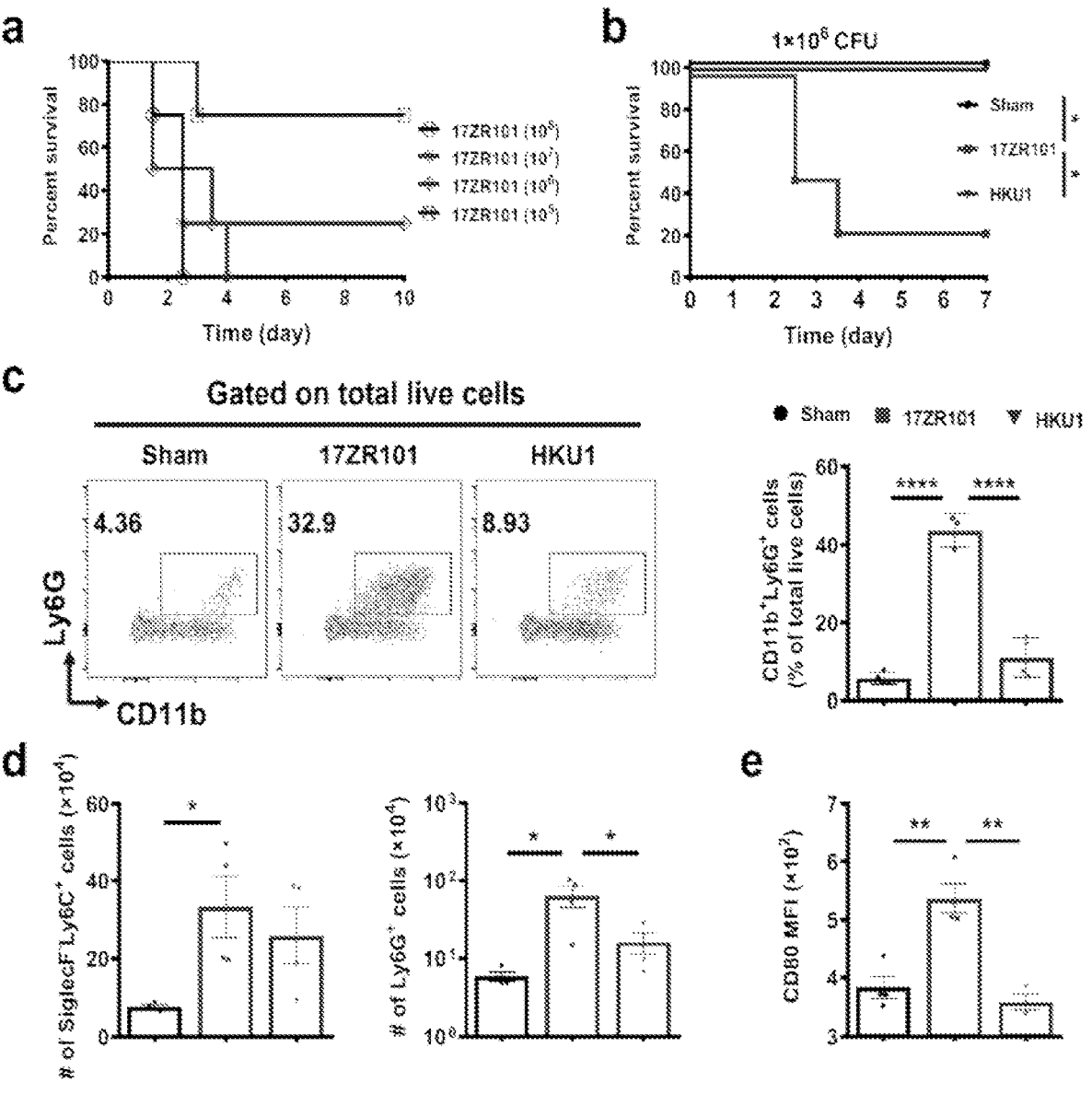
FIG. 10 depicts experimental results showing HvKp induces neutrophil recruitment and M1 polarization in mouse pneumonia model. (a) C57BL6 mice were inoculated with indicated dose of hvKp by nasal drops and the survival curve was recorded. (b) Survival of mice intranasally challenged by ~$10^6$ CFU Kp strains or sham-infected during a seven-day period. (c) Representative flow cytometric plots and quantification of Neus collected from the lungs of infected mice. (d) Quantification of IMs and Neus in lung cells were performed. (e) The mean fluorescence intensity (MFI) of M1 marker CD80 on the surface of IMs. *p<0.05, p<0.01, *p<0.001, ****p<0.0001.

To validate this data from scRNA-seq, we analyzed the changes in the amount and types of immune cells and signaling molecules of the immune system in the lungs of mice infected by 17ZR101, and observed markedly increased infiltration of IMs and Neus in these organs (FIG. 3a). The infiltrated IMs were also found to express higher levels of CD80 proteins at their surface, indicating that the proinflammatory M1 polarization process has been enhanced (FIG. 3b). It should be noted that M1 polarization was not found in HKU1-infected animals, yet infiltration of IMs was still observed in the lungs of HKU1-infected mice (FIG. 3b). These immune responses were recapitulated in a more clinically relevant pneumonia model (FIG. 10).

To investigate how hvKp infection alters the transcription patterns of lung cells, high-throughput RNA sequencing (RNA-seq) analysis of total RNA isolated from the lung tissues of hvKp- and cKp-infected mice was performed. The number of genes that were significantly up-regulated (n=651) or down-regulated (n=372) in 17ZR101-infected mice, when compared to Sham-infected mice, was recorded (FIG. 3c). Gene ontology analyses depicted cytokine production, cell chemotaxis, and extracellular matrix organization during infection by 17ZR101 (FIG. 3d), confirming that hvKp infection triggered strong inflammatory responses in the host. Activation of cytokine production by Kp in a mouse pneumonia model was found to result in increase in the level of inflammatory factors as well as M1 polarization. Consistently, increased expression of pro-inflammatory and neutrophils activation markers (FIG. 3e) as well as chemokines, interleukins, and PRRs was observed (FIG. 11a). Enhanced production of such pro-inflammatory molecules was further confirmed by RT-qPCR (FIG. 11b). In addition, 17ZR101-infected mice exhibited up to 100-fold increase in the level of serum interleukin (IL)-6, interferon (IFN)-γ and IL-1β (FIG. 3f). Taken together, these findings confirmed the flow cytometry data in that 17ZR101 induced M1 polarization and neutrophil chemotaxis, which is characteristic of a cytokine storm.

HvKp-Induced Cytokine Storm was Mediated by the STAT1 Pathway

Figure 4:
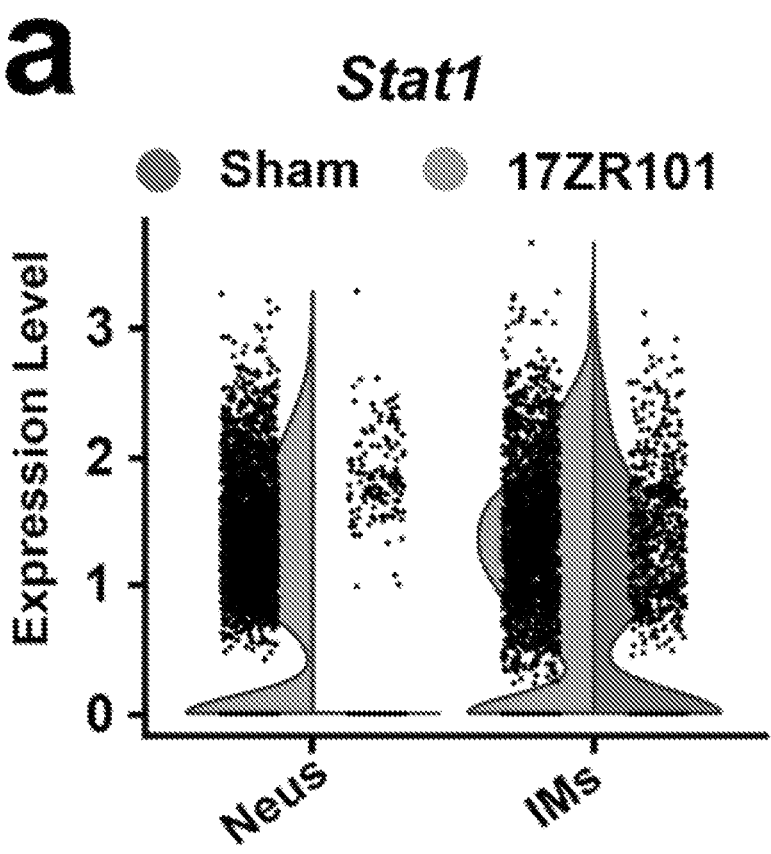
FIG. 4 depicts data showing inhibition of STAT1 protects mice from lethal hvKp infection. (a) Expression of Stat1 in Neus and IMs was identified by scRNA-Seq. (b) C57BL6 mice were inoculated with $10^4$ CFU of indicated Kp strains and lung sample lysates were prepared for immunoblotting at 12 hpi. Beta actin was used as a loading control and the expression level of proteins detected by immunoblotting were quantified by normalizing to beta actin. (c) Representative of histogram and MFI change of p-STAT1 on IMs and Neus were shown. (d) Total lung cells from Sham- and 17ZR101-infected mice (12 hpi) were cultured with activation cocktail. After 4 h of culture, cells were harvested and intracellular staining was performed (IFN-γ), and cytokine-producing NK1.1$^+$ cells were analyzed by flow cytometry. (e) Quantification of IFN-γ production in NK1.1$^+$ cells. (f) Survival rate of 17ZR101-infected mice treated with F-ara at 3 hpi. n=10. (g) Analysis of serum IFN-γ levels of mice treated with F-ara. n=5. *p<0.05, ****p<0.0001.
Figure 4:
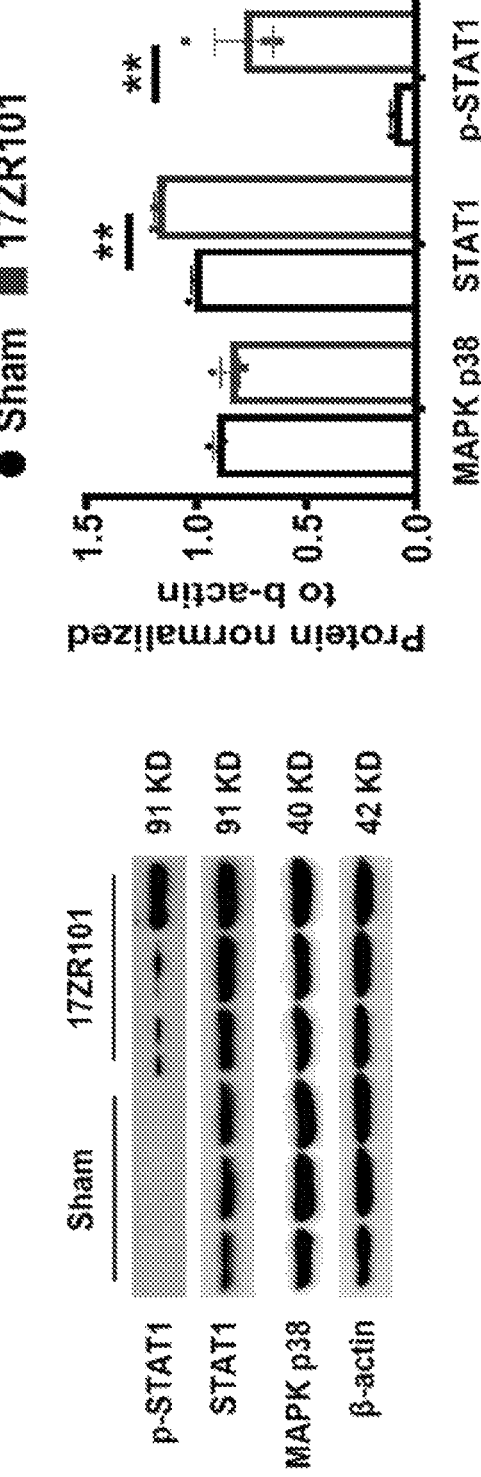
Figure 4:
Figure 12:
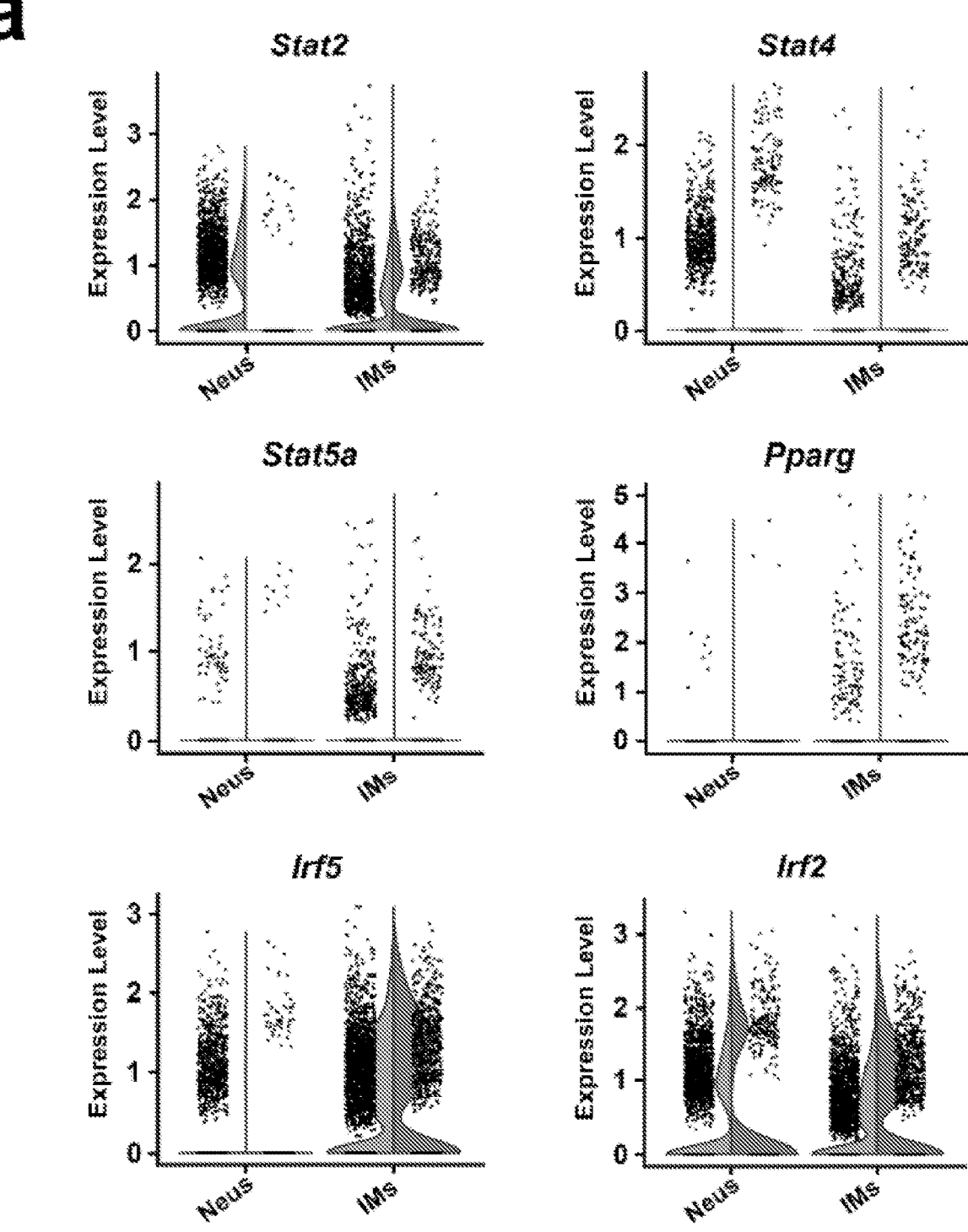
FIG. 12 depicts experimental results showing transcriptional regulation of M1 polarization. (a) Expression of Stat2, Stat5a, Stat4, Pparg, Irf5 and Irf2 in Neus and IMs were identified by scRNA-Seq. (b) Heatmap of transcription factors involved in macrophage polarization. (c) Fold-change in gene counts of Ifna, Ifnar1, Stat1, and Ifng in 17ZR101-compared with Sham- and HKU1-infected lung cells as determined by RNA-seq. n=5.

Macrophage polarization is known to be regulated by various transcription factors including STAT, NF-κB, interferon-regulatory factor (IRF), peroxisome proliferator-activated receptor (PPAR-γ), and cAMP-responsive element-binding protein (CREB). Among these factors, expression of Stat1 (Log 2 fold change: 2.700), Stat2 (1.834), Irf1(2.309), Irf5 (1.069), and Irf7 (3.152) was found to increase dramatically upon 17ZR101 infection, indicating that these pathways became active during infection (FIG. 12a, b). IRFs are regulators of type I IFN (−α and −β) expression and signaling, and STAT2 also plays a role in type I IFN-mediated anti-viral and anti-proliferative signaling. However, expression of type I IFNs could not be detected by RNA-Seq or qRT-PCR (Ifnb was not detected in scRNA-Seq and RNA-Seq, FIG. 12c). Importantly, STAT1 was proven to be a pivotal mediator of M1 macrophage polarization in the presence of IFN-γ; the qPCR result confirmed a 5.2-fold increase in expression of Stat1 (FIG. 12c). More convincingly, scRNA-Seq revealed that Stat1 was highly expressed in 17ZR101-infected Neus and IMs (FIG. 4a), suggesting that STAT1 might function as a regulator in 17ZR101-induced M1 polarization and neutrophil activation, resulting in the expression of pro-inflammatory cytokines To confirm the STAT1 expression and the source of IFN-γ, we evaluated the level of STAT1 expression by western blotting and found that STAT1 was up-regulated in the lung tissues of 17ZR101-infected mice. Unexpectedly, phosphorylated STAT1 (p-STAT1) was only detectable in 17ZR101-infected animals but not in sham-group (FIG. 4 b). Further analysis confirmed that STAT1 was phosphorylated in infected IMs and Neus (FIG. 4c). Flow cytometric analysis also revealed that NK cells were a major source of IFN-γ upon 17ZR101 infection (FIG. 4d, e). These findings indicated both up-regulated STAT1 biosynthesis and phosphorylation contributed to hvKp-induced M1 polarization and neutrophil infiltration. To further confirm the role of STAT1 in the pathogenesis of hvKp infection, mice were infected with 17ZR101 and then intraperitoneally administrated with Fludarabine (F-ara), an effective inhibitor of STAT1. F-ara treatment was found to be able to protect 50% mice from death due to 17ZR101 infection within 48 h (FIG. 4f), and significantly reduce the serum IFN-γ level (445.133 pg mL⁻¹ vs 2742.872 pg mL⁻¹) (FIG. 4g). Together, these results confirmed that hvKp-induced cytokine storm was partially STAT1-dependent.

Acetylsalicylic Acid Alleviates Cytokine Storm Induced by hvKp Infection

To further confirm whether induction of onset of a cytokine storm in the host is a key process of hvKp pathogenesis, we tested the therapeutic value of other immune suppressants or non-steroidal anti-inflammatory drugs (NSAIDs) on hvKp-infected mice. At 48 hpi, treatment with acetylsalicylic acid (aspirin or ASA), was able to protect 100% of the mice infected by 17ZR101, all of which would have died within 24 hpi without such treatment (FIG. 5a). In addition, ASA treatment was also able to alleviate bodyweight loss (2.076% vs 7.206%) (FIG. 5b) and reduce the spleen/body weight ratio (0.495% vs 0.863%) at 12 hpi (FIG. 5c). ASA treatment was found to be associated with suppressed F4/80⁺ cells infiltration into the lungs (FIG. 5d) and able to inhibit M1 macrophage polarization during hvKp infection (FIG. 5e), but with a slight decrease in the levels of neutrophils in the lungs. Results of RNA-Seq and qPCR further confirmed the decrease in expression level of M1 macrophage markers upon administration of ASA (FIG. 5f, g). It should also be noted that the protective effect conferred by ASA could suppress the cytokine storm and drastically reduce serum IL-6 production (57.964 pg mL⁻¹ vs 587.965 pg mL⁻¹) (FIG. 5h). Importantly, ASA treatment was found to significantly inhibit Stat1 expressions (−1.056) and down-regulate expression of three STAT1-regulated chemokines, namely Cxcl9 (−2.118), Cxcl10 (−3.590) and Cxcl11(−2.098) (FIG. 5f), confirming that STAT1 is a key transcriptional factor involved in hvKp-induced IMs polarization and Neus recruitment, and then initiation of the cytokine storm during hvKp infection.

Other immunosuppressants such as naproxen (NPXS), dexamethasone (DXMS), azathioprine (AzA), and cyclosporine A (CsA) could protect up to 60% of mice from death due to 17ZR101 infection, yet cyclophosphamide (CTX) did not exhibit any protective effect (FIG. 5a). Taken together, these data confirmed that hvKp-induced mortality was largely attributed to the cytokine storm elicited during the infection process.

Combination of Aspirin and CAZ-AVI Rescues the Mice in Acute hvKp Infection

Figure 6:
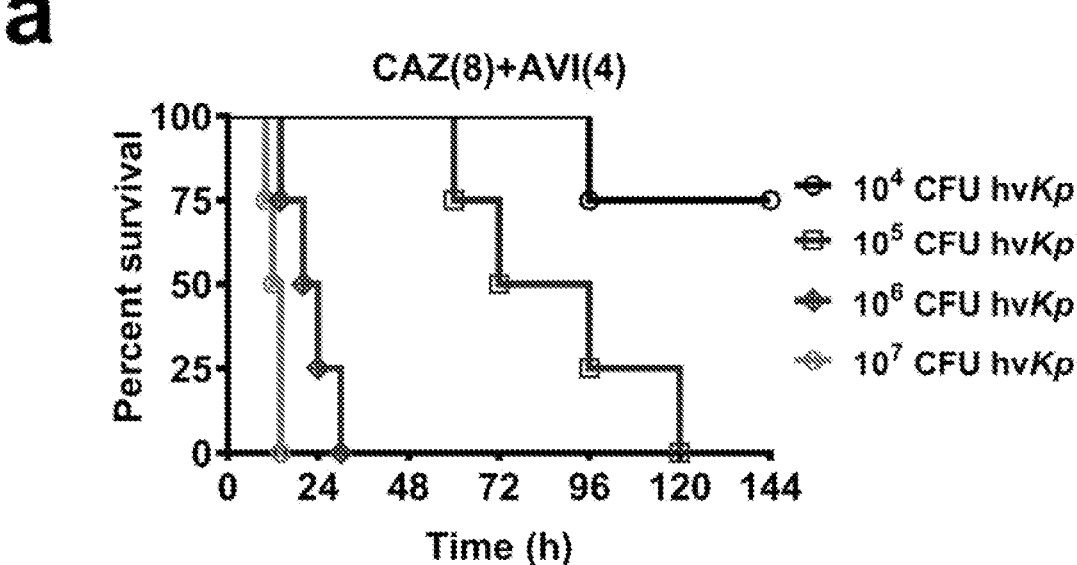
FIG. 6 depicts data demonstrating combination of ASA and CAZ/AVI provides protection for mice in the cytokine storm induced by acute hvKp infection. (a) The Kaplan-Meier survival curve of mice infected by indicated dose of hvKp and treated with fixed dose of CAZ-AVI. n=5. (b) Survival curve of mice infected with $10^7$ hvKp and these mice were given PBS, CAZ-AVI, ASA and CAZ/AVI+ASA at 1 hpi. n=8. (c) Quantification of CD11b$^+$F4/80$^+$ and CD11b$^+$Ly6G$^+$ in infected lungs analyzed by flow cytometry at 4 hpi. (d) Bacteria burden of various organs from mice infected by $10^7$ hvKp and treated with drugs at 4 hpi. NS, not significant; *p<0.05, p<0.01, *p<0.001, ****p<0.0001.
Figure 6:
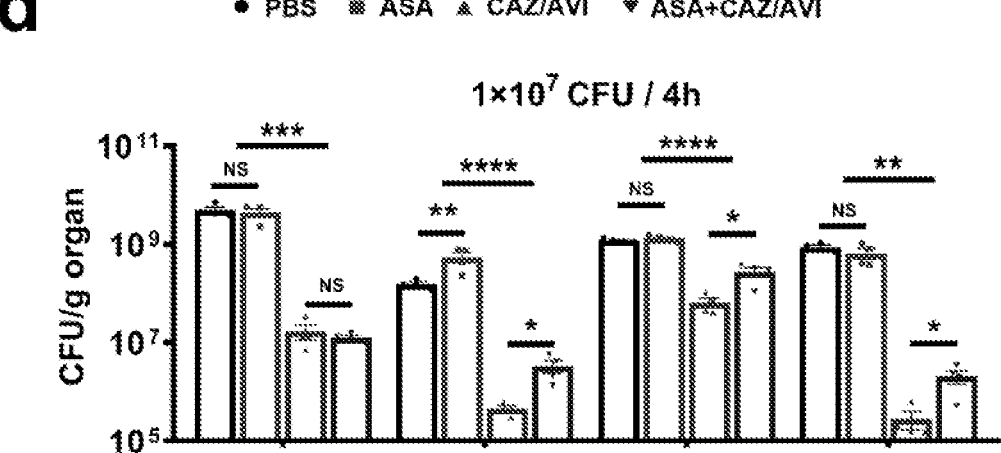

To explore a new therapeutic strategy with the mice under acute hvKp infection, a combination of ASA and antibiotics was employed in acute hvKp infection. The fixed-dose antimicrobial combination ceftazidime-avibactam (CAZ-AVI) consists of a third-generation cephalosporin and a novel synthetic β-lactamase inhibitor, approved in 2015 by the US Food and Drug Administration for the treatment of complicated intraabdominal infections and complicated urinary infections. The combination of CAZ and AVI could not prevent mice from death until CAZ (8 mg kg$^{-1}$)-AVI (4 mg kg$^{-1}$) by hvKp infection (FIG. 13*a, b*). However, when the mice underwent an acute Kp infection (~$10^7$ CFU), antibiotic (CAZ (8 mg kg$^{-1}$)-AVI (mg kg$^{-1}$) alone failed to protect mice from death, with the mice all died within 14 h (FIG. 6*a*). Surprisingly, the combination of ASA (100 mg kg$^{-1}$) and CAZ (8 mg kg$^{-1}$)-AVI (4 mg kg$^{-1}$) robustly rescued mice form death within 24 h, suggesting the synergistic anti-inflammatory drugs and antibiotics is both required for this process (FIG. 6*b*). To unveil the underlying mechanism of the therapeutic effect of combination of ASA and CAZ-AVI, the changes in the amount and types of immune cells in the lungs of mice infected by 17ZR101 and bacteria burdens in various organs at 4 hpi were analyzed. These results showed that ASA could suppress F4/80$^+$ cells infiltration but not significantly on Ly6G$^+$ cells, at the same time without contributing to bacteria clearance, indicating an anti-inflammation role of ASA administration (FIG. 6*c, d*). Meanwhile, antibiotic (CAZ-AVI) alone could not protect mice form death although bacteria burden could be readily reduced by CAZ-AVI administration (FIG. 6*d*). However, the combination of ASA and CAZ-AVI was still not able to protect infected mice from death with an increasing bacteria load at 24 hpi compared with 4 hpi (FIG. 6*b*; FIG. 13*c*). Together, these results confirmed that the combination of anti-inflammatory drugs and antibiotics was more efficient in acute hvKp infection.

Figure 5:
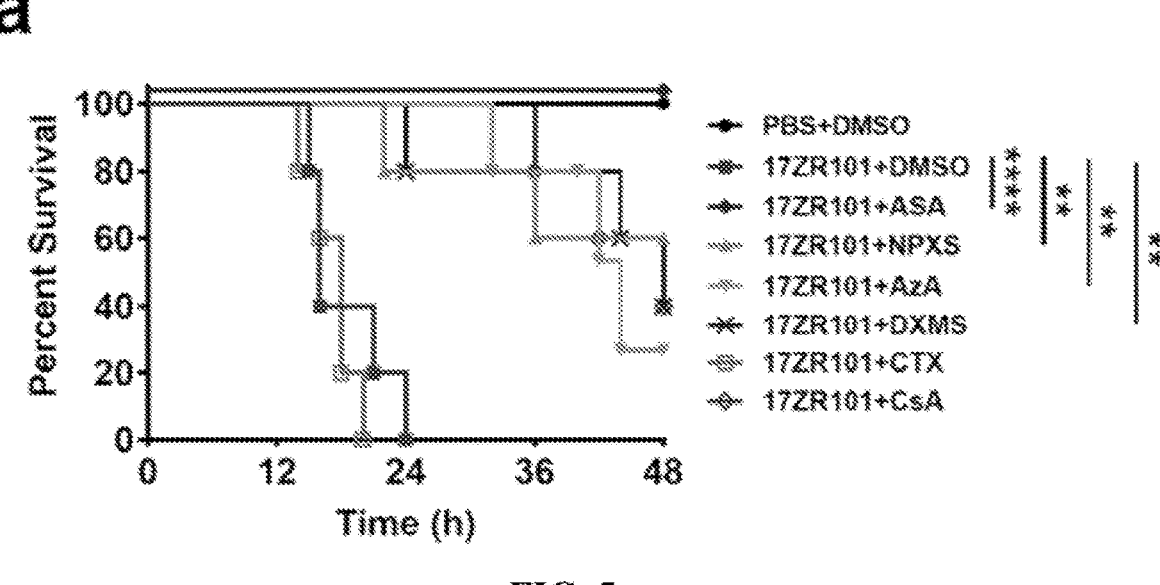
FIG. 5 depicts data demonstrating ASA suppresses the cytokine storm induced by hvKp. (a) C57BL6 mice were inoculated with $10^4$ CFU of indicated Kp strains and various therapeutic drugs were administrated at 3 hpi. The Kaplan-Meier survival curve of mice was recorded. n=5. (b) The loss in body weight of mice treated with drugs at 12 hpi. n=5-10. (c) Weight of spleen normalized to body weight and representative images of spleens harvested from Sham, 17ZR101, and 17ZR101+ASA treated mice, n=10. (d) Flow cytometry analysis of IMs and Neus in total lung cells. (e) Quantification of IMs in lungs and CD80 MFI on the surface of F4/80$^+$ cells. (f) Comparative analysis of individual gene transcript expression in indicated groups for M1 markers. n=3. (g) Fold-change in expression level of genes related to macrophage polarization and inflammation in lung cells of 17ZR101+ASA-treated mice, with lung cells of Sham- and 17ZR101-treated mice as control. n=5. (h) Quantification of serum IL-6 levels measured by ELISA kit. *p<0.05, p<0.01, *p<0.001, ****p<0.0001.
Figure 5:
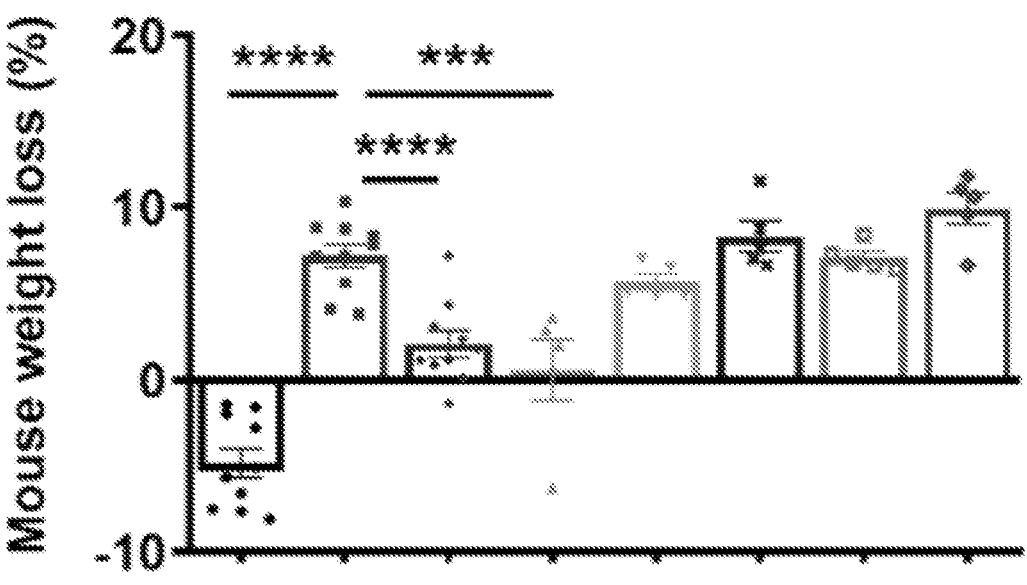
Figure 5:
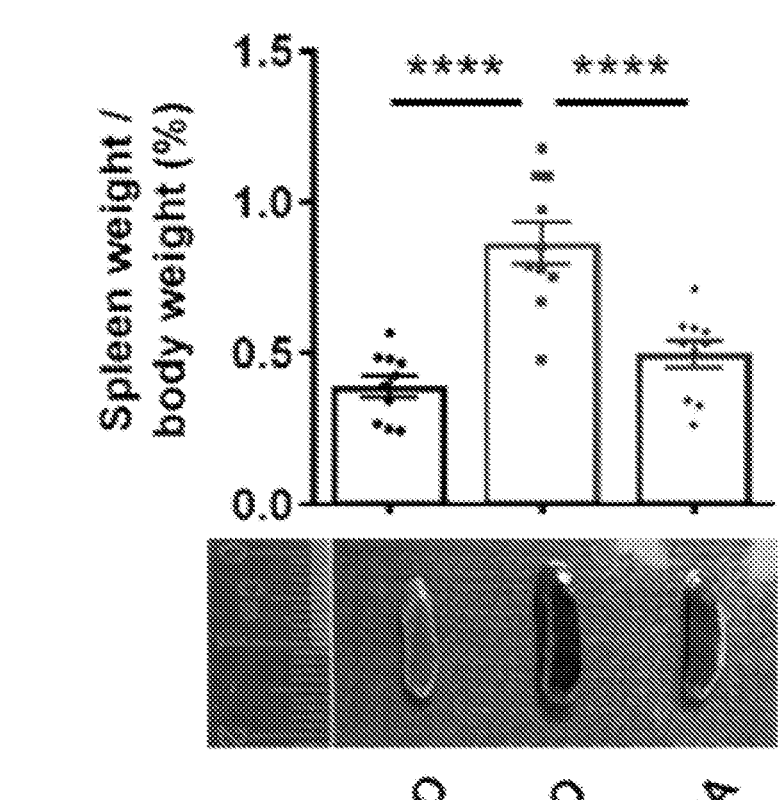
Figure 5:
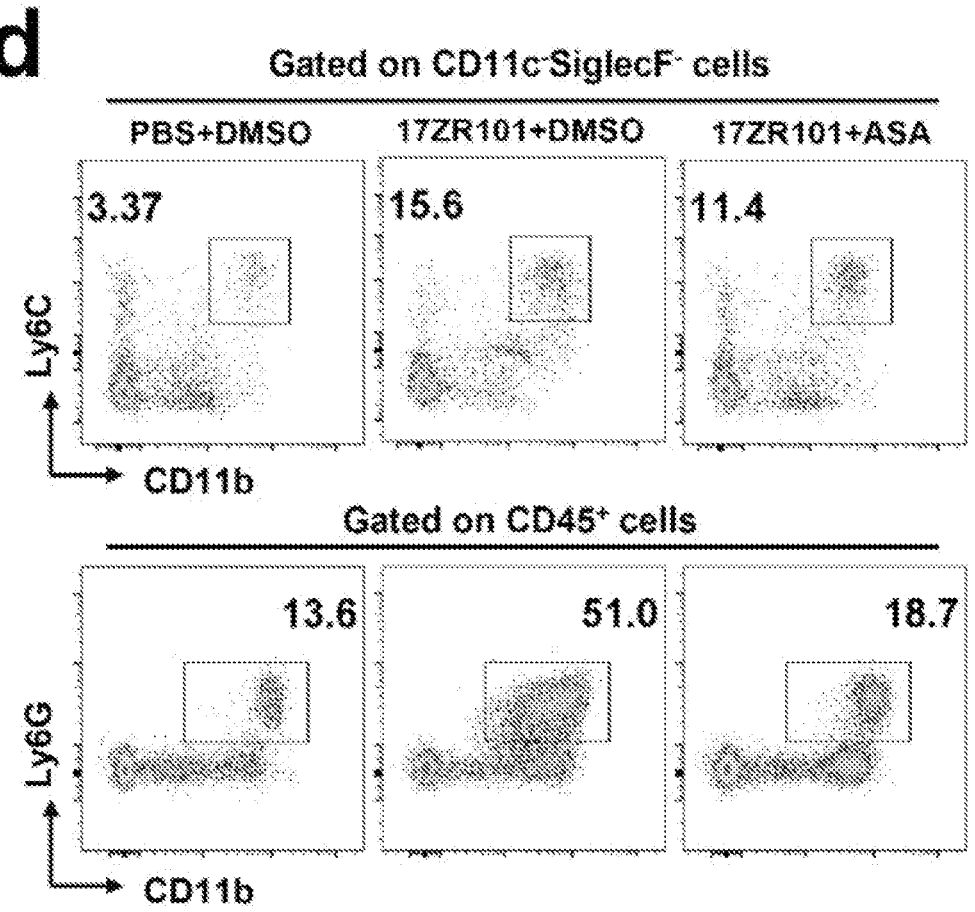
Figure 5:
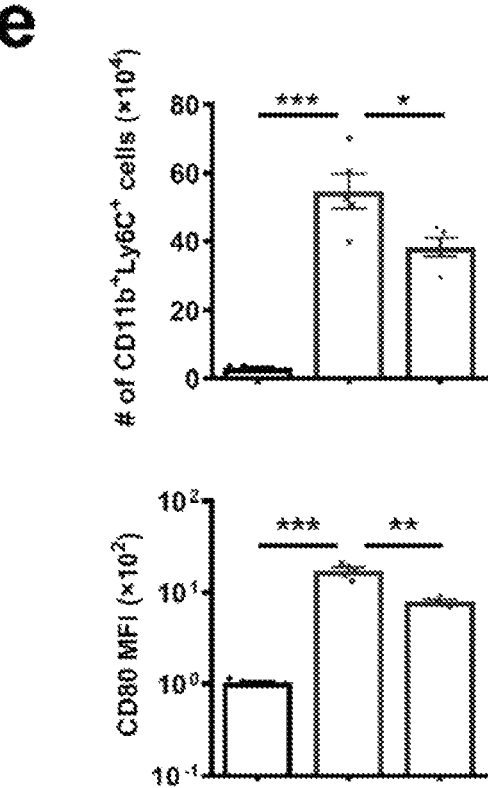
Figure 5:
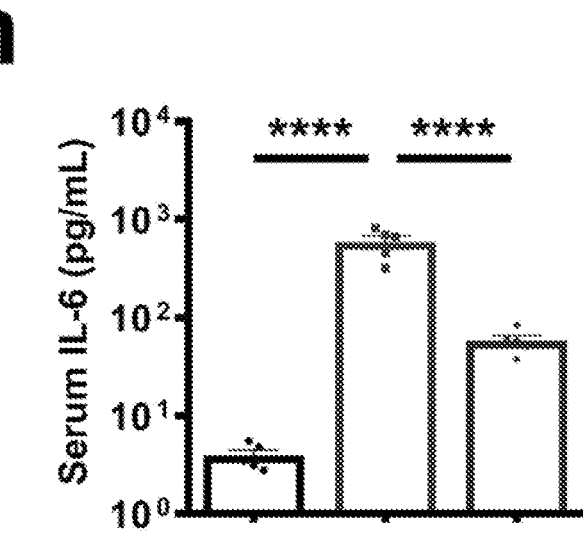

The present disclosure investigates why hvKp infection is often associated with high mortality. Unlike cKp which can be readily cleared by host defense system during infection, hvKp exhibits resistance to host killing and is therefore able to continuously stimulate the host immune response during the infection process. The data shows that persistence of the hvKp strain in the host triggers the onset of a cytokine storm through activation of the STATS pathway. The cytokine storm eventually leads to septic shock, which has a high risk of death. In this work, it is shown that this hvKp-triggered cytokine storm could be suppressed by immune-suppressants, such as aspirin (FIG. 5). The M1 polarization is involved in protection against acute infections; yet uncontrolled activation of M1 macrophages activation may be responsible for causing the disease symptoms during Kp infection. These results showed that hvKp induced excessive M1 polarization and neutrophil infiltration. However, this infiltration did not result in hvKp clearance, indicating that hvKp could co-exist with phagocytes. It was therefore concluded that the ability to resist killing by phagocytes is the underlying mechanism by which hvKp exhibits high level virulence and a high potential of causing death of the host during infection. This unique feature of hvKp is attributed to the abundance of capsule and the large number of siderophore systems possessed by such strains. It was reported that hvKp strains produce a very thick capsule that effectively protects the bacterium from the hostile environment, and various siderophores that help acquire iron from iron-depleted environments. In particular, aerobactin contributes to better growth and survival of hvKp in vivo. In hvKp strain 17ZR101, the capsule regulator rmpC and the aerobactin-coding genes iucABCD are located in the virulence plasmid. These results showed that the virulence plasmid is essential for the survival and pathogenesis of hvKp (FIG. 1). Several other studies also demonstrated that neutrophil extracellular traps (NETs) escaping and neutrophil-mediated phagocytosis resistance also contributed to the ability of hvKp to resist killing by phagocytes. Based on the results disclosed herein, it was found that hvKp was partially internalized but not eradicated, confirming that hvKp developed a defensive mechanism that can modulate phagocytosis and suppress killing by the immune cells of the host. Consistently, a previous study showed that Kp actively manipulated phagosome maturation and phagolysosome fusion to its advantage.

Cytokine storm is a fast-developing, life-threatening clinical condition in which over-production of inflammatory cytokines and excessive activation of immune cells cause a range of damage in the host, with high risk of death if left untreated. To date, hvKp-induced cytokine storm has not been reported. On the other hand, cytokine storm is known to be associated with infections caused by influenza and various other viruses, bacteria, or fungi, with sepsis being a condition commonly associated with onset of cytokine storm. Multiple reports suggested that secretion of IL-1β may cause formation of cytokine storm in patients infected by SARS-COV and MERS-COV. It is known that IL-1β is mainly secreted by macrophages upon apoptosis and pyroptosis. A recent study also reported that the H7N9 influenza virus could activate the gasdermin E-mediated pyroptosis process and triggered formation of a lethal cytokine storm. Similarly, Kp infection was also found to cause macrophage pyroptosis via secretion of outer membrane vesicles. Notably, results of RNA-Seq analysis in this work also showed that hvKp infection caused increased expression of genes (Nlrp3, Caspase-1, Caspase-11, Gsdmd, and Il1b) involved in pyroptosis (data not shown). However, whether pyroptosis is directly involved in onset of septic shock during hvKp infection, and the detailed regulatory mechanisms concerned, entails further investigation.

Aspirin is an affordable, globally available drug that inhibits the cyclooxygenase-1 enzyme, which controls the production of thromboxane A2 and proinflammatory prostaglandins. Aspirin has been shown to prevent in vitro hyperactivity of platelets in patients infected by SARS-COV-2, inhibit intravascular coagulation in *Staphylococcus* sepsis, and reduce sepsis-related mortality in patients. Consistently, it was found that ASA treatment suppressed the cytokine storm that developed during hvKp infection and increased the survival rate of mice suffering from hvKp-induced sepsis. ASA treatment has also been reported to inhibit M1 macrophage polarization upon LPS treatment by suppressing both the IκK/IκB/NF-κB pathway and the COX2/PGE2/EP2/NF-κB positive feedback loop. However, no significant difference in the level of Cox-1 and Cox-2 expression at the mRNA level upon ASA administration was found. Instead, it was found that Stat1 expression was suppressed by ASA treatment, indicating that STAT1 may be a potential target for effective treatment of sepsis. Importantly, the effect of treatment with the STAT1 inhibitor fludarabine resembled that of ASA. To conclude, findings in this work explain why hvKp infections are associated with a high death rate and confirm that the STAT1 pathway is an excellent target for development of effective treatment of life-threatening bacterial and viral infections, including but not limited to those caused by hvKp.

Materials and Methods

Bacterial Strains

Two clinical *K. pneumoniae* isolates (17ZR101 and HKU1) were used in this study. Strain 17ZR101 was recovered from a 43-year-old female patient in the ICU of The Second Affiliated Hospital of Zhejiang University in 2017. The patient had undergone a tracheostomy and then subjected to tracheal intubation. She then developed symptoms of infection and *K. pneumoniae*. strain 17ZR101 was isolated from the secretion fluid of tracheal intubation. The patient was treated with meropenem and tigecycline and recovered eventually. Strain HKU1 was isolated from a blood sample of a patient in a hospital in Hong Kong. The species identity of these strains determined by the Vitek 2 system (bioMérieux, France) and confirmed by the MALDI-TOF MS apparatus (Bruker, Germany). Phenotypic characterization and whole genome sequencing was conducted on these two strains. A string test was then performed by stretching bacterial colonies grown on sheep blood agar plate through the use of an inoculation loop.

Whole Genome Sequencing

Strain 17ZR101 and HKU1 were subjected to whole genome sequencing to identify the virulence genes and antibiotic resistance genes that they harbored. Multilocus sequence typing (MLST) was determined by the Kleborate software based on the types of genetic variations in the seven housekeeping genes (https://github.com/katholt/Kleborate). Capsular typing on the assembled sequences was performed using Kaptive[1]. Virulence genes were identified by searching against the BIGSdb *Klebsiella* genome database (http://bigsdb.pasteur.fr/*klebsiella/klebsiella*.html). The genotypes of the two strains are listed in FIG. 7.

Antibiotic Susceptibility Test

The antimicrobial susceptibility of the two *Klebsiella* strains was determined by the microdilution method according to the guidelines recommended by the Clinical and Laboratory Standards Institute[2]. *Escherichia coli* strain ATCC 25922 was included as a quality control strain. All tests were performed in duplicate, and each test included three biological replicates.

Generation of Virulence Plasmid-Cured Strain and Conjugation Assay

Plasmid-cured strain 17ZR101-PC was generated from 17ZR101 by following a previously described protocol[3]. To screen for the virulence plasmid-cured strain, tellurite sensitivity assay was performed, followed by PCR test to determine if the marker gene rmpA2 in the virulence plasmid was not present. The MIC profiles of the transconjugants were also determined for differentiation between transconjugants and the donor strains. Conjugation was also performed by using virulence plasmid harboring *E. coli* transconjugant 16ZR187-TC1 as donor and 17ZR101-PC as recipients. MacConkey agar plates containing 4 μg mL$^{-1}$ K$_2$TeO$_3$ and 1 μg mL$^{-1}$ meropenem were used to select transconjugants. The presence of rmpA2 as a marker gene of virulence plasmid in transconjugants was determined by PCR. To further confirm that the virulence plasmid had been cured and acquisition of virulence plasmid by 17ZR101-PC, S1 and XbaI-nuclease pulsed-field gel electrophoresis (XbaI-PFGE) were performed.

Animal Experiments

All animal experiments were approved by the Animal Ethics Committee of the City University of Hong Kong and followed the guidelines of the Institutional Laboratory Animal Research Unit. Six- to eight-weeks-old animals of both sexes were used in this study. For the sepsis model, mice were intravenously injected with ~10$^4$ colony forming units (CFU) of the test stain resuspended in 200 μL PBS. For the pneumonia model, mice were anesthetized by inhaling isoflurane, and ~10$^6$ CFU of the strain resuspended 10 μL PBS were dripped into the mouse's nasal cavity. The heads of the mice were hold upright for 30 s afterwards.

Preparation of Cells from Lung and Spleen

Cells collected from different tissues of the test animals were subjected to flow cytometry analysis as described previously[4]. Cells from spleens were obtained by mashing the organ through a 70-μm cell strainer and collected in a tube containing RPMI 1640 medium supplemented with 5% fetal bovine serum. To prepare lung cells, lung tissues were excised and incubated in HBSS containing 1×HEPES and Collagenase type I. The tissue fragments were forced through a 70-μm strainer as described above. Red blood cells were lysed with ACK lysing buffer.

Measurement of Bacterial Burden in Various Organs of the Test Animals

Ten-fold dilutions of tissue homogenate were prepared and spread onto MacConkey agar plates containing 2 μg mL$^{-1}$ cefotaxime to determine the bacterial load in different organs of the infected animals. To determine the number of intracellular bacteria, cells prepared for flow cytometry from lungs and spleens were collected and then incubated with 300 μg mL$^{-1}$ amikacin to kill the extracellular bacteria. The number of total and intracellular bacteria was counted and presented as the number of CFU g$^{-1}$ tissue.

Single-Cell Sample Preparation, Data Preprocessing and Cell-Type Determination Cell suspension prepared by collagenase digestion and mashing against cell strainer was sent to BGI TECH SOLUTIONS (HONGKONG) CO., LIMITED for sequencing. Routine procedures including sample processing, library generation, cleaned data filtration, and alignment were performed by BGI. Analysis of scRNA-seq data was performed using the package Seurat (version 4.1.1). We retain valid cells based on number of genes, mitochondrial RNA percentage and number of UMIs (unique molecular identifiers. The raw counts were then normalized, and highly variable genes were calculated in all datasets with default parameters. We performed Seurat's standard data integration process based on the identification of anchor cells between the two data sets. After integration, data scaling, PCA, dimensionality reduction (using UMAPs) and clustering were applied for cluster identification and data visualization. Differential expression analysis (DEA) for all clusters was performed to determine their marker genes. Marker gene of all clusters were selected based on a normalized RNA expression value. that being >0.25 log-fold higher than the mean expression value in the other sub-clusters, and with a detectable expression in >25% of all cells from the corresponding cells. To assign identities of clusters, we listed the established lung cell types with classical markers and RNA markers and then annotated the refined clusters. Raw sequencing reads are available at the NCBI Gene Expression Omnibus (GEO) under the accession numbers GSE220594.

RNA Extraction and Real-Time Quantitative PCR Analysis

RNA was extracted from lung samples by homogenization in TRIzol reagent (15596026, Thermo Fisher Scientific), followed by chloroform extraction and isopropanol precipitation. The extracted RNA was reverse-transcribed into cDNA by using a SuperScript® III First-Strand Synthesis SuperMix kit (11752050, ThermoFisher Scientific). Real-time quantitative PCR was performed by using a QuantStudio™ 7 Pro Real-Time PCR System, following the manufacturer's instructions. cDNA samples were tested in duplicates, and the relative amount of mRNA in different samples (Gapdh, Il1b, Ifng, Cxcl2, Cxcl10, Ifna, Ifnb, Ifnar1, Stat1, Hmgb1, Il-6, Myd88, and Tlr4) was determined by the comparative threshold cycle (ΔΔCT) method, using the glyceraldehyde-3-phosphate dehydrogenase gene (Gapdh) for normalization.

Cytokine Analysis

The serum level of IL-6 of the test animals was measured by using the IL-6 Mouse Uncoated ELISA Kit (Thermo fisher scientific, 88-7064-88), IL-1β level by IL-1 beta Mouse Uncoated ELISA Kit (Thermo fisher scientific, 88-7013-86) and that of IFN-γ was measured by using the IFN gamma Mouse Uncoated ELISA Kit (Thermo fisher scientific, 88-7314-88) according to instructions of the manufacturer.

Flow Cytometry

Dead cells were excluded from the analysis by propidium iodide (Sigma-Aldrich Corporation, P4170-1G) or ghost Dye™ violet 510 (Tonbo Biosciences, 13-0870-T100) staining in all flow cytometry experiments. Fluorescently labeled mAbs against mouse CD45, CD11b, CD206, CD80, Ly6G, CD11c, SiglecF, Ly6C and appropriate isotype controls were obtained from Biolegend. For intracellular cytokine measurement, cells were incubated with Cell Activation Cocktail (BioLegend, 423303) at 37° C. in the dark for 4 h. Anti-IFN-γ-PE antibody (eBioscience, 12-7177-81) was used to determine intracellular expression of IFN-γ. For p-STAT1 measurement, the cells were fixed with IC fixation buffer (eBioscience, 00-8222-49) for 30 min and then suspended in 1 mL of methanol to permeabilize the cell membrane, left to stand for 10 min on ice. At the time of p-STAT1 measurement, the cell suspensions were washed with FACS buffer and then stained with PE-anti-STAT1 Phospho antibody (Biolegend, 686404). Flow cytometric analyses were performed using a BD FACSCelesta™ flow cytometer (BD Bioscience). The acquired data were analyzed by the FlowJo software (Version 10.0.7, Treestar, Palo Alto, CA).

Western Blotting

The lung tissues of the test animals were homogenized in lysis buffer, which contained RIPA buffer, protease, and phosphatase inhibitor (Roche). Protein concentration was measured by performing the Bradford Assay (Bio-Rad Laboratories). Briefly, 10 μL of the cell lysates were resolved by standard 12% SDS-PAGE gel and electroblotted onto 0.2 mm nitrocellulose membrane (Bio-Rad) using a semi-dry transfer unit (Bio-Rad). The membranes were blocked with 5% milk in TBST for 1 h at room temperature, and then incubated overnight at 4° C. with the following primary antibodies diluted in 5% BSA in TBST. Primary antibodies against STAT1 (1:4000, #9172T), phospho-STAT1 (1:4000, #7649T) and MAPK p38 (1:4000, #8690T) were obtained from Cell Signaling Technologies. β-actin (1:4000, #ab119716) was obtained from Abcam. Immunoreactive bands were visualized by incubation with goat anti-rabbit immunoglobulins (1:5000, Abcam, #ab205718). Each experiment was repeated at least twice.

Tissue Preparation and Processing for Imaging

Tissues of the lungs and livers of the test animals were placed in a cold saline solution and rinsed immediately after they were collected. The tissues were fixed in 4% paraformaldehyde, dehydrated, and embedded in paraffin prior to sectioning at 5 μm and staining with hematoxylin and eosin. Several pulmonary hematoxylin and eosin staining images were randomly selected for pathological scoring in a blinded fashion. For cryosections, tissues were sequentially incubated with 20% and 30% sucrose and subsequently embedded in OCT compound. We obtained 8-10-μm-thick cryosections using a cryostat.

RNA-Seq Analysis

Total RNA was extracted from lung samples by homogenization in TRIzol reagent, followed by chloroform extraction and isopropanol precipitation. DNA was removed by DNase treatment (TURBO DNA-Free™ Kit). RNA samples were sent to Novogene (HK) Company Limited for sequencing. Routine procedures of mRNA purification and library generation were performed by Novogene. Sequencing reads alignment was performed by using HISAT2. Count aligned reads and quantification were calculated based on exon regions using FeatureCounts. Significantly changed genes (FPKM≥1 in either Sham-, 17ZR101-, HKU1-, or 17ZR101+ASA-treatment group, Log 2Fold Change>1, padj<0.01) were identified by DESeq2 analysis. Gene Set Enrichment Analysis was performed for gene ontology enrichment analysis. The raw RNA-seq data has been deposited in NCBI database under the accession number PRJNA851242.

Drug Treatment

In ASA, NPXS, CTX, AzA, CsA, DXMS, and F-ara treatment experiment, mice challenged by 17ZR101 were given intraperitoneally 100 mg $kg^{-1}$ ASA, 50 mg $kg^{-1}$ NPXS, 150 mg $kg^{-1}$ CTX, 200 mg $kg^{-1}$ AzA, 20 mg $kg^{-1}$ CsA, 10 mg $kg^{-1}$ DXMS and 40 mg $kg^{-1}$ F-ara at 3 hpi, another group treated with an equal volume of PBS or 200 μL of corn oil solution was included as a control group. In ASA and CAZ/AVI combination treatment experiment, mice were given intraperitoneally 100 mg $kg^{-1}$ ASA plus 8 mg $kg^{-1}$ CAZ and 4 mg $kg^{-1}$ AVI or 8 mg $kg^{-1}$ CAZ and 4 mg $kg^{-1}$ AVI at 1 hpi. The health status and weight of all mice were observed and recorded.

Statistical Analysis

Statistical analysis of data obtained in this work was performed by means of Graphpad Prism 6.0 (GraphPad Software, La Jolla California USA, www.graphpad.com). Statistical analyses on normally distributed data sets were performed using one-way ANOVA with Tukey's correction for multiple comparisons. The log-rank test was used for comparing survival rate in animal experiments. P values <0.05 was considered significant. Unless otherwise indicated, the survival curve of mice in animal experiments and results of flow cytometry analysis were representative of at least two independent experiments.

REFERENCES

Addin En. Reflist

1 Wyres, K. L. et al. Identification of *Klebsiella* capsule synthesis loci from whole genome data. *Microbial genomics* 2 (2016).

2 Wayne, P. A. Clinical and Laboratory Standards Institute: Performance standards for antimicrobial susceptibility testing: 20th informational supplement. *CLSI document M100-S20* (2010).

3 El-Mansi, M., Anderson, K. J., Inche, C. A., Knowles, L. K. & Platt, D. J. Isolation and curing of the *Klebsiella pneumoniae* large indigenous plasmid using sodium dodecyl sulphate. *Research in microbiology* 151, 201-208 (2000).

4 Yang, G. et al. Pik3c3 deficiency in myeloid cells imparts partial resistance to experimental autoimmune encephalomyelitis associated with reduced IL-1β production. *Cellular & Molecular Immunology* 18, 2024-2039 (2021).

What is claimed is:

1. A method of treating a hypervirulent *Klebsiella pneumoniae* (hvKp) infection in a subject in need thereof, the method comprising co-administering a therapeutically effective amount of an antibiotic and a signal transducer and activator of transcription 1 (STAT1) inhibitor to the subject, wherein the antibiotic is a carbapenem or a cephalosporin.

2. The method of claim 1, wherein the hvKp comprises a pLVPK-like virulence plasmid or a pK2044-like virulence plasmid.

3. The method of claim 1, wherein the hvKp comprises one or more carbapenemase genes selected from the group consisting of $bla_{KPC-2}$, $bla_{VIM}$, $bla_{IMP}$, $bla_{OXA-48}$, $bla_{SPM}$, $bla_{AIM}$, $bla_{DIM}$, $bla_{GIM}$, $bla_{SIM}$, and $bla_{NDM-1}$.

4. The method of claim 2, wherein the hvKp comprises one or more carbapenemase genes selected from the group consisting of $bla_{KPC-2}$, $bla_{VIM}$, $bla_{IMP}$, $bla_{OXA-48}$, $bla_{SPM}$, $bla_{AIM}$, $bla_{DIM}$, $bla_{GIM}$, $bla_{SIM}$, and $bla_{NDM-1}$.

5. The method of claim 1, wherein the hvKp infection causes increased expression in the subject of one or more genes selected from the group consisting of Nlrp3, Caspase-1, Caspase-11, Gsdmd, and Il1b.

6. The method of claim 1, wherein the STAT1 inhibitor is epigallocatechin-3 gallate, nifuroxazide, fludarabine, or a pharmaceutically acceptable salt thereof.

7. The method of claim 1, wherein the antibiotic is cefotaxime, cefpodoxime, ceftizoxime, ceftriaxone, ceftazidime, cefoperazone, cefepime, cefozopran, cefpirome, cefquinome, ceftobiprole, ceftaroline, ceftolozane, or a pharmaceutically acceptable salt thereof.

8. The method of claim 1 further comprising the step of co-administering a β-lactamase inhibitor.

9. The method of claim 8, wherein the β-lactamase inhibitor is sulbactam, tebipenem, clavulanic acid, tazobactam, avibactam, relebactam, vaborbactam, or a pharmaceutically acceptable salt thereof.

10. The method of claim 1, wherein the hvKp comprises one or more of a pLVPK-like virulence plasmid and a carbapenemase genes selected from the group consisting of $bla_{KPC-2}$, $bla_{VIM}$, $bla_{IMP}$, $bla_{OXA-48}$, $bla_{SPM}$, $bla_{AIM}$, $bla_{DIM}$, $bla_{GIM}$, $bla_{SIM}$, and $bla_{NDM-1}$;

and the method further comprises co-administering avibactam or a pharmaceutically acceptable salt thereof.

11. The method of claim 1, wherein the method further comprises the step of providing a sample comprising the hvKp or suspected of comprising the hvKp from the subject; and determining whether the hvKp comprises one or more of a pLVPK-like virulence plasmid and a carbapenemase genes selected from the group consisting of $bla_{KPC-2}$, $bla_{VIM}$, $bla_{IMP}$, $bla_{OXA-48}$, $bla_{SPM}$, $bla_{AIM}$, $bla_{DIM}$, $bla_{GIM}$, $bla_{SIM}$, and $bla_{NDM-1}$ prior to the step of co-administering a therapeutically effective amount of the antibiotic and the STAT1 inhibitor to the subject.

\* \* \* \* \*